(12) United States Patent
Weiss et al.

(10) Patent No.: US 9,365,647 B2
(45) Date of Patent: Jun. 14, 2016

(54) COMPOUNDS FOR USE IN THE TREATMENT OF ALZHEIMER'S DISEASE

(71) Applicants: Stefan Franz Thomas Weiss, Johannesburg (ZA); Katarina Jovanovic, Edenvale (ZA); Danielle Gonsavles, Johannesburg (ZA); Bianca Da Costa Dias, Johannesburg (ZA); Stefan Knackmuss, Plankstadt (DE); Uwe Reusch, Maikammer (DE); Melvyn Little, St. Peter-Ording (DE); Marc Saul Weinberg, Midrand (ZA)

(72) Inventors: Stefan Franz Thomas Weiss, Johannesburg (ZA); Katarina Jovanovic, Edenvale (ZA); Danielle Gonsavles, Johannesburg (ZA); Bianca Da Costa Dias, Johannesburg (ZA); Stefan Knackmuss, Plankstadt (DE); Uwe Reusch, Maikammer (DE); Melvyn Little, St. Peter-Ording (DE); Marc Saul Weinberg, Midrand (ZA)

(73) Assignee: UNIVERSITY OF THE WITWATERSRAND, JOHANNESBURG, Johannesburg (SA)

( * ) Notice: Subject to any disclaimer, the term of this patent is extended or adjusted under 35 U.S.C. 154(b) by 0 days.

(21) Appl. No.: 14/345,770

(22) PCT Filed: Sep. 19, 2012

(86) PCT No.: PCT/IB2012/054968
§ 371 (c)(1),
(2) Date: Mar. 19, 2014

(87) PCT Pub. No.: WO2013/042053
PCT Pub. Date: Mar. 28, 2013

(65) Prior Publication Data
US 2014/0220041 A1 Aug. 7, 2014

(30) Foreign Application Priority Data
Sep. 19, 2011 (ZA) .................................. 2011/06804

(51) Int. Cl.
C07K 16/28 (2006.01)
A61K 31/7105 (2006.01)
A61K 39/395 (2006.01)
C12N 15/113 (2010.01)
C07K 16/26 (2006.01)

(52) U.S. Cl.
CPC ............ *C07K 16/26* (2013.01); *A61K 31/7105* (2013.01); *A61K 39/3955* (2013.01); *C12N 15/1138* (2013.01); *C07K 2317/76* (2013.01)

(58) Field of Classification Search
None
See application file for complete search history.

(56) References Cited

U.S. PATENT DOCUMENTS

| 7,507,797 B2 * | 3/2009 | Knackmuss et al. ....... 530/387.9 |
| 2007/0041977 A1 * | 2/2007 | Knackmuss et al. ....... 424/146.1 |
| 2011/0136892 A1 * | 6/2011 | Flavell et al. ............... 514/44 A |

OTHER PUBLICATIONS

Pflanz 2009 "The 37kda/67kda laminin receptor LRP/LR as a molecular target in neurodegenerative diseases" Dissertation, Ludwig-Maximilians—Universitat Munich Germany.*
Previtali 2003 "expression of laminin receptors in schwann cell differentiation: evidence for distinct roles" J neurosci 23(13):5520-5530.*
Yow 1988 "increased mRNA expression of a laminin-binding protein in human colon carcinoma: complete sequence of a full-length cDNA encoding the protein" PNAS 85:6394-6398.*
International Search Report dated May 23, 2013 for Application No. PCT/IB2012/054968.
Office Action dated Sep. 0, 2015 for Application No. EP 12 780 543.0.
Vana, K., et al., "LRP/LR as an Alternative Promising Target in Therapy of Prion Diseases, Alzheimer's Disease and Cancer", Infectious Disorders—Drug Targets, 9, 2009, pp. 69-80.
Leucht, C., et al., "The 37 kDa/67 kDa laminin receptor is required for PrP$^{sc}$ propagation in scrapie-infected neuronal cells", EMBO Reports, vol. 4, No. 3, 2003, pp. 290-295.
Vana, K.,"The 37 kDa/67 kDa laminin receptor as a therapeutic target in prion diseases: potency of antisense LRP RNA, siRNAs specific for LRP mRNA and a LRP decoy mutant", Dissertation zur Erlangung des Doktorgrades der Fakultat fur Chemie und Pharmazie der Ludwig-Maximilians—Universitat Munchen, 2006, pp. 1-127.
Leucht, C., et al., "Knock-down of the 37-kDa/67-kDa lanlinin receptor in mouse brain by transgenic expression of specific antisense LRP RNA", Transgenic Research 13, 2004, pp. 81-85.
Rey, C., "Single Chain Antibodies Against the KDA/67 KDA Laminin Receptor as Tools for Prion Diseases Therapy", Dissertation zur Erlangung des Doktorgrades der Fakultat fur Chemie und Pharmazie der Ludwig·Maximilians—Universitat Munchen, 2005, pp. 1-122.
Da Costa Dias, B., et al., "Structural and mechanistic commonalities of amyloid-β and the prion protein", Prion, 2011, pp. 126-137.
Mafune, K., et al., "Anti-sense RNA of 32-kDa Laminin-Binding Protein Inhibits Attachment and Invasion of a Human Colon Carcinoma Cell Line", Journal of Surgical Research, 52, 1992, pp. 340-346.
Miller, V., et al., "Targeting Alzheimer's disease genes with RNA interference: an efficient strategy for silencing mutant alleles", Nucleic Acids Research, vol. 32, No. 2, 2004, pp. 661-668.
Nillsson, P., et al., Gene therapy in Alzheimer's disease—potential for disease modification:, J. Cell. Mol. Med., vol. 14, No. 4, 2010, pp. 741-757.
Chen, S., et al., "Current Experimental Therapy for Alzheimer's Disease", Current Neuropharmacology, 5, 2007, pp. 172-134.
Ludewigs, H., et al., "Therapeutic approaches for prion disorders", Expert Rev. Anti . Infect. Ther., 5(4), 2000, pp. 613-630.

* cited by examiner

*Primary Examiner* — Adam W Weidner
(74) *Attorney, Agent, or Firm* — Ladas & Parry LLP

(57) ABSTRACT

The invention relates to a method of modulating concentration of Alzheimer's Disease (AD) relevant proteins amyloid precursor protein (APP), beta (β) and gamma (γ) secretases and amyloid beta peptide (Aβ), and also relates to a method of reducing Aβ shedding. Furthermore, this invention extends to a compound for use in the treatment of AD, and also to a method of treating AD.

4 Claims, 14 Drawing Sheets

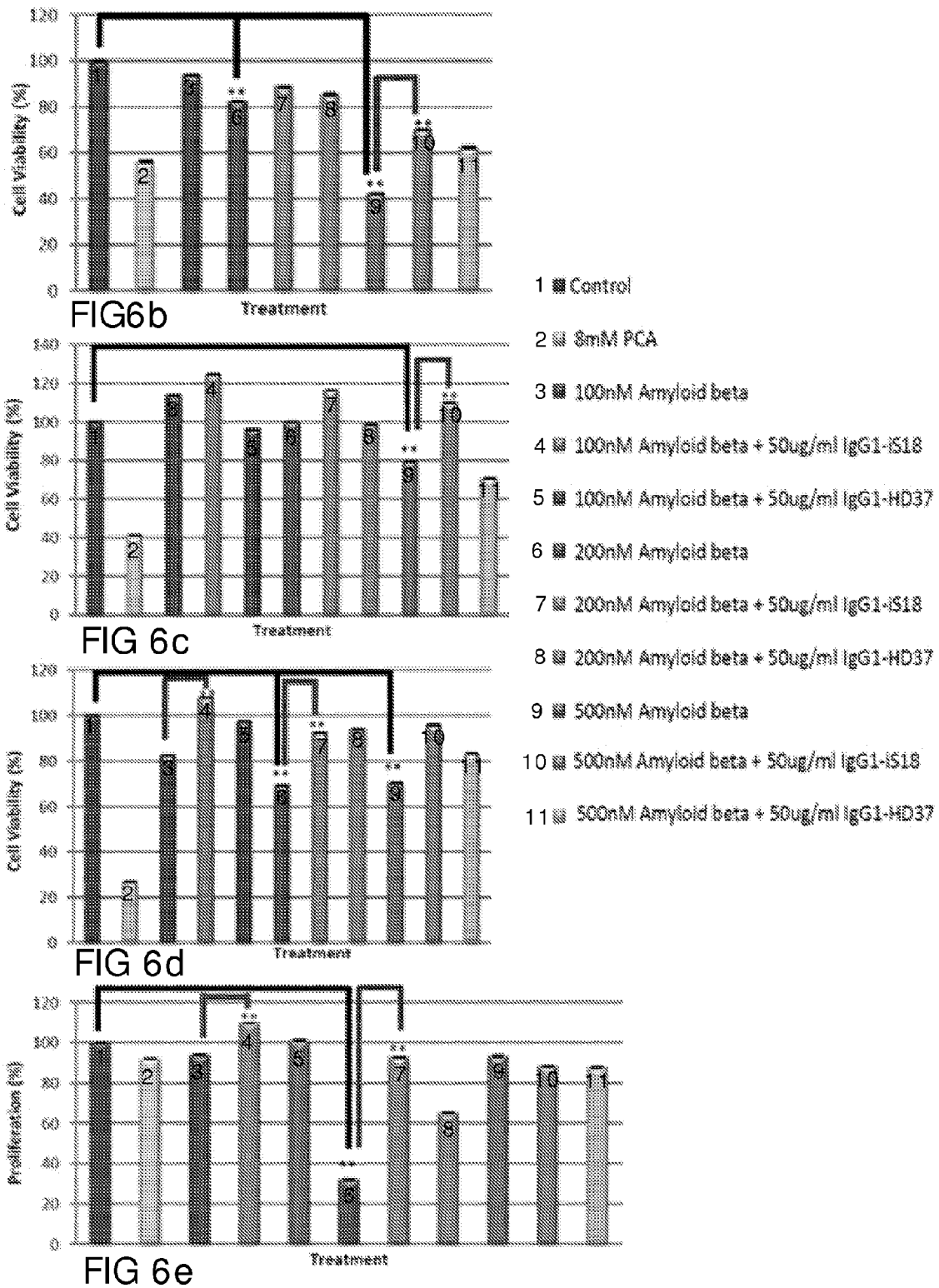

COMPOUNDS FOR USE IN THE TREATMENT OF ALZHEIMER'S DISEASE

FIELD OF INVENTION

This invention relates to a compound for the modulation of 37 kDa/67 kDa laminin receptor in humans and/or animals. The invention extends to a method of modulating concentration of Alzheimer's Disease (AD) relevant proteins amyloid precursor protein (APP), beta (β) and gamma (γ) secretases and amyloid beta peptide (Aβ). Furthermore, this invention extends to a compound for use in the treatment of AD, and also to a method of treating AD.

BACKGROUND

Alzheimer's disease (AD) is notably the most prevalent form of dementia afflicting the elderly and is associated with a multitude of genetic, environmental, epigenetic, dietary and lifestyle risk factors[1]. AD is said to affect in excess of 37 million people globally[4].

The neuropathological hallmarks of AD include intracellular neurofibrillary tangle formation and extracellular amyloid beta peptide (Aβ) plaque deposition[5]. The sequential cleavage of the amyloid precursor protein (APP) by beta (β) and gamma (γ) secretases[2] results in the shedding of the 4 kDa Aβ which aggregates to form amyloid plaques. Aβ, as a soluble oligomer, as well as plaque-incorporated aggregate, is the predominant focus of investigative efforts to treat AD.

Aβ and more specifically the 42 amino acid isoform ($A\beta_{42}$), is largely considered the primary disease causing agent in AD (as Aβ accumulation is a pre-requisite for tau hyperphosphorylation, another AD-associated protein)[6]. Specifically, Aβ is generated through the proteolytic cleavage of the type I transmembrane protein APP by β- and γ-secretase. The mechanisms underlying Aβ induction of neuronal loss (one of the key pathophysiological features of AD) are yet to be firmly established. It is proposed that the neurotoxicity of Aβ is partially mediated through its interactions with cellular receptors. These interactions may include binding of Aβ to a surface receptor on a neuron thereby changing its biochemical structure, which negatively affects neuronal communication. It is proposed that Aβ may affect neuronal communication by eliciting alterations in signal transduction pathways through direct binding to cell surface receptors, (such as N-methyl-d-aspartate (NMDA) receptors, insulin receptors, α-7 nicotinic receptors)[3,7]. Alternatively, Aβ may alter signal transduction pathways indirectly via incorporation into lipid membranes of the plasma membrane and, to a lesser extent, cellular organelles[8]. This is thought to induce structural and functional alterations in lipid bound receptors and consequently results in aberrant signal transduction pathways[8].

There is a need for compounds which in use modulate the production and concentrations of APP, (β) and (γ) secretases and Aβ in a human or animal in order to treat AD. There is a further need for compounds that modulate intracellular neurofibrillary tangle formation and extracellular Aβ plaque deposition in order to treat AD.

SUMMARY

According to a first aspect of this invention there is provided a method for reducing concentration of at least one Alzheimer's Disease (AD) relevant protein selected from the group including, but not limited to, amyloid precursor protein (APP), beta (β) and gamma (γ) secretases and amyloid beta peptide (Aβ), the method comprising contacting a cell surface protein, preferably an extracellular matrix glycoprotein, with a cell surface protein specific antibody, preferably a monoclonal antibody, or any fragment of the aforementioned, such that binding occurs between a surface epitope of the cell surface protein and the cell surface protein specific antibody causing a decrease in the concentration of the at least one AD relevant proteins.

The reduction in Aβ concentration may be a reduction relative to Aβ concentration in a normal healthy human or animal, or it may be a reduction relative to Aβ concentration in a human or animal suffering from AD.

It is to be understood that the binding between the surface epitope of the cell surface protein and the cell surface protein specific antibody at least hinders, preferably prevents, binding of the at least one AD relevant proteins to the cell surface protein.

The cell surface protein may be a laminin receptor protein. In a preferred embodiment of the invention the laminin receptor is 37 kDa/67 kDa laminin receptor (LRP/LR) of a human and/or animal. LRP/LR is also known as LAMR, RPSA and p40. The cell surface protein may also be a protein showing at least 80% or greater homology to the laminin receptor protein, preferably showing at least 80% or greater homology to LRP/LR.

In a preferred embodiment of the invention the AD relevant protein whose concentration is reduced via the method of this invention is Aβ. The reduced amount of Aβ causes reduced intracellular neurofibrillary tangle formation and/or reduced extracellular Aβ plaque deposition in human and/or animal cells, preferably neuronal cells, therein treating and/or preventing AD.

The cell surface protein specific antibody may be any antibody, or fragment thereof, raised against the cell surface protein. In a preferred embodiment the antibody is raised against LRP/LR or against a protein having 80% or greater homology with LRP/LR. The antibody, or fragment thereof, may be a F(ab')2 fragment, a Fab fragment scFv, a bi-specific scFv, a tri-specific scFv, a single chain or tandem diabody, a single domain antibody (dAb), a minibody or a molecular recognition unit (MRU). Furthermore, the antibody, or fragment thereof, may be monovalent, bivalent or multivalent. The antibody, or fragment thereof, may additionally comprise at least one further antigen-interaction site and/or at least one further effector domain.

In a preferred embodiment of the invention, the antibody or fragment thereof may be an anti-laminin receptor specific antibody, preferably an anti-LRP/LR specific antibody, further preferably IgG1-iS18.

In a preferred embodiment of the invention the cell surface protein and/or the cell surface protein specific antibody is a human or animal cell surface protein and/or cell surface protein specific antibody. The cell surface protein may be located on murine neuronal cells (N2a), human neuronal cells (SH-SY5Y), baby hamster kidney cells (BHK) and human embryonic kidney cells (HEK293 and/or HEK293 FT).

In a preferred embodiment of the invention, the method for reducing concentration of at least one AD relevant protein selected from the group including, but not limited to, APP, beta (β) and gamma (γ) secretases and Aβ, the method comprises contacting LRP/LR with IgG1-iS18, or any fragment thereof, such that binding occurs between LRP/LR and IgG1-iS18, or any fragment thereof, causing a decrease in the concentration of Aβ.

According to a second aspect of this invention there is provided a method for reducing amyloid beta peptide (Aβ) shedding caused by the proteolytic cleavage of amyloid precursor protein (APP) by beta (β) and gamma (γ) secretases, the method comprising contacting a cell surface protein, preferably an extracellular matrix glycoprotein, with a cell surface protein specific antibody, preferably a monoclonal antibody, or any fragment of the aforementioned, such that binding occurs between a surface epitope of the cell surface protein and the cell surface protein specific antibody therein hindering the proteolytic cleavage of APP by beta (β) and gamma (γ) secretases.

The reduction in Aβ shedding may be a reduction relative to Aβ shedding in a normal healthy human or animal, or it may be a reduction relative to Aβ shedding in a human or animal suffering from AD.

It is to be understood that the binding between the surface epitope of the cell surface protein and the cell surface protein specific antibody at least hinders, preferably prevents, binding of at least one of the AD relevant proteins APP, beta (β) and gamma (γ) secretases and Aβ to the cell surface protein. It is to be understood that this binding causes a reduction in Aβ shedding.

The cell surface protein may be a laminin receptor protein. In a preferred embodiment of the invention the laminin receptor is 37 kDa/67 kDa laminin receptor (LRP/LR) of a human and/or animal. LRP/LR is also known as LAMR, RPSA and p40. The cell surface protein may also be a protein showing at least 80% or greater homology to the laminin receptor protein, preferably showing at least 80% or greater homology to LRP/LR.

The cell surface protein specific antibody may be any antibody, or fragment thereof, raised against the cell surface protein. In a preferred embodiment the antibody is raised against LRP/LR or against a protein having 80% or greater homology with LRP/LR. The antibody, or fragment thereof, may be a F(ab')2 fragment, a Fab fragment scFv, a bi-specific scFv, a tri-specific scFv, a single chain or tandem diabody, a single domain antibody (dAb), a minibody or a molecular recognition unit (MRU). Furthermore, the antibody, or fragment thereof, may be monovalent, bivalent or multivalent. The antibody, or fragment thereof, may additionally comprise at least one further antigen-interaction site and/or at least one further effector domain.

In a preferred embodiment of the invention, the antibody or fragment thereof may be an anti-laminin receptor specific antibody, preferably an anti-LRP/LR specific antibody, further preferably IgG1-iS18.

In a preferred embodiment of the invention the cell surface protein and/or the cell surface protein specific antibody is a human or animal cell surface protein and/or cell surface protein specific antibody. The cell surface protein may be located on murine neuronal cells (N2a), human neuronal cells (SH-SY5Y), baby hamster kidney cells (BHK) and human embryonic kidney cells (HEK293 and/or HEK 293 FT).

In a preferred embodiment of the invention, the method for reducing Aβ shedding caused by the proteolytic cleavage of APP by beta (β) and gamma (γ) secretases, the method comprises contacting LRP/LR with IgG1-iS18, or any fragment thereof, such that binding occurs between LRP/LR and IgG1-iS18, or any fragment thereof, causing a reduction in Aβ shedding.

According to a third aspect of this invention there is provided a method for reducing concentration of at least one Alzheimer's Disease (AD) relevant protein selected from the group including, but not limited to, amyloid precursor protein (APP), beta (β) and gamma (γ) secretases and amyloid beta peptide (Aβ), the method comprising contacting a cell surface protein, preferably an extracellular matrix glycoprotein, with a nucleotide sequence, preferably an RNA sequence, further preferably a short hairpin RNA (shRNA) sequence or a short interfering RNA (siRNA) sequence or a micro RNA (miRNA) sequence, such that binding occurs between mRNA of the cell surface protein and the nucleotide sequence causing a downregulation of the cell surface protein which in turn causes a decrease in the concentration of the at least one AD relevant proteins.

It is to be understood that the binding between the mRNA of the cell surface protein and the nucleotide sequence downregulates the cell surface protein such that there are fewer cell surface proteins present on the cell when compared to regular physiological functioning. Therefore, there are fewer binding sites available for the at least one AD relevant proteins to bind to. A reduction in binding sites leads to reduced concentrations of the at least one AD relevant proteins APP, beta (β) and gamma (γ) secretases and Aβ.

The cell surface protein may be a laminin receptor protein. In a preferred embodiment of the invention the laminin receptor is 37 kDa/67 kDa laminin receptor (LRP/LR) of a human and/or animal. LRP/LR is also known as LAMR, RPSA and p40. The cell surface protein may also be a protein showing at least 80% or greater homology to the laminin receptor protein, preferably showing at least 80% or greater homology to LRP/LR.

Preferably, when binding between the nucleotide sequence and the mRNA occurs, such binding is between the nucleotide sequence and LRP mRNA.

In a preferred embodiment of the invention the AD relevant protein whose concentration is reduced via the method of this invention is Aβ. The reduced amount of Aβ causes reduced intracellular neurofibrillary tangle formation and/or reduced extracellular Aβ plaque deposition in human and/or animal cells, preferably neuronal cells, therein treating and/or preventing AD. The reduction in Aβ concentration may be a reduction relative to Aβ concentration in a normal healthy human or animal, or it may be a reduction relative to Aβ concentration in a human or animal suffering from AD.

The nucleotide sequence is preferably shRNA, further preferably at least one of shRNA1 and shRNA7 having sequence listing as set forth in SEQ ID NO: 1 and 2, respectively.

In a preferred embodiment of the invention the cell surface protein and/or the nucleotide sequence is a human or animal cell surface protein and/or nucleotide sequence. The cell surface protein may be located on murine neuronal cells (N2a), human neuronal cells (SH-SY5Y), baby hamster kidney cells (BHK) and human embryonic kidney cells (HEK293 and/or HEK 293 FT).

In a preferred embodiment of the invention, the method for reducing concentration of at least one AD relevant protein selected from the group including, but not limited to, APP, beta (β) and gamma (γ) secretases and Aβ, the method comprises contacting LRP mRNA with shRNA1 and/or shRNA7 having sequence listing as set forth in SEQ ID NO: 1 and 2, respectively, such that binding occurs between the LRP mRNA and shRNA1 and/or shRNA7 causing a decrease in the concentration of Aβ.

According to a fourth aspect of this invention there is provided a method for reducing Aβ shedding caused by the proteolytic cleavage of amyloid precursor protein (APP) by beta (β) and gamma (γ) secretases, the method comprising contacting a cell surface protein, preferably an extracellular matrix glycoprotein, with a nucleotide sequence, preferably an RNA sequence, further preferably a short hairpin RNA (shRNA) sequence or a short interfering RNA (siRNA) sequence or a micro RNA (miRNA) sequence, such that binding occurs between mRNA of the cell surface protein and the nucleotide sequence causing a downregulation of the cell surface protein which in turn causes a decrease in the proteolytic cleavage of APP by beta (β) and gamma (γ) secretases.

The reduction in Aβ shedding may be a reduction relative to Aβ shedding in a normal healthy human or animal, or it may be a reduction relative to Aβ shedding in a human or animal suffering from AD.

It is to be understood that the binding between the mRNA of the cell surface protein and the nucleotide sequence downregulates the cell surface protein such that there are fewer cell surface proteins present on the cell when compared to regular physiological functioning. Therefore, there are fewer binding sites available for the at least one AD relevant proteins to bind to. A reduction in binding sites leads to a reduction in Aβ shedding.

The cell surface protein may be a laminin receptor protein. In a preferred embodiment of the invention the laminin receptor is 37 kDa/67 kDa laminin receptor (LRP/LR) of a human and/or animal. LRP/LR is also known as LAMR, RPSA and p40. The cell surface protein may also be a protein showing at least 80% or greater homology to the laminin receptor protein, preferably showing at least 80% or greater homology to LRP/LR.

Preferably, when binding between the nucleotide sequence and the mRNA occurs, such binding is between the nucleotide sequence and LRP mRNA.

The nucleotide sequence is preferably a shRNA, further preferably at least one of shRNA1 and shRNA7 having sequence listing as set forth in SEQ ID NO: 1 and 2, respectively.

In a preferred embodiment of the invention the cell surface protein and/or the nucleotide sequence is a human or animal cell surface protein and/or nucleotide sequence. The cell surface protein may be located on murine neuronal cells (N2a), human neuronal cells (SH-SY5Y), baby hamster kidney cells (BHK) and human embryonic kidney cells (HEK293 and/or HEK 293 FT).

In a preferred embodiment of the invention, the method for reducing Aβ shedding caused by the proteolytic cleavage of APP by beta (β) and gamma (γ) secretases, the method comprises contacting LRP mRNA with shRNA1 and/or shRNA7 having sequence listing as set forth in SEQ ID NO: 1 and 2, respectively, such that binding occurs between LRP mRNA and shRNA1 and/or shRNA7 reducing LRP/LR cell surface levels causing a reduction in Aβ shedding.

According to a fifth aspect of this invention there is provided a method for reducing concentration of at least one Alzheimer's Disease (AD) relevant protein selected from the group including, but not limited to, amyloid precursor protein (APP), beta (β) and gamma (γ) secretases and amyloid beta peptide (Aβ), the method comprising contacting a cell surface protein of the first aspect of the invention with the antibody of the first aspect of the invention and the nucleotide sequence of the third aspect of the invention.

According to a sixth aspect of this invention there is provided a method for reducing Aβ shedding caused by the proteolytic cleavage of amyloid precursor protein (APP) by beta (β) and gamma (γ) secretases, the method comprising the method comprising contacting a cell surface protein of the second aspect of the invention with the antibody the second aspect of the invention and the nucleotide sequence of the fourth aspect of the invention.

According to a seventh aspect of this invention there is provided for use of an anti-laminin receptor specific antibody in the manufacture of a pharmaceutical composition to treat Alzheimer's Disease (AD).

In a preferred embodiment of the invention the anti-laminin receptor specific antibody may be anti-37 kDa/67 kDa laminin receptor (LRP/LR) specific antibody, further preferably the anti-LRP/LR specific antibody may be IgG1-iS18.

According to an eighth aspect of this invention there is provided an anti-laminin receptor specific antibody for use in treating Alzheimer's Disease (AD). In a preferred embodiment of the invention the anti-laminin receptor specific antibody may be anti-37 kDa/67 kDa laminin receptor (LRP/LR) specific antibody, further preferably the anti-LRP/LR specific antibody may be IgG1-iS18.

According to a ninth aspect of this invention there is provided for use of a nucleotide sequence in the manufacture of a pharmaceutical composition to treat Alzheimer's Disease (AD).

In a preferred embodiment of the invention the nucleotide sequence may be a shRNA, further preferably at least one of shRNA1 and shRNA7 having sequence listing as set forth in SEQ ID NO: 1 and 2, respectively. The use may further include an anti-laminin specific receptor antibody, preferably an anti-LRP/LR specific antibody, further preferably IgG1-iS18.

According to a tenth aspect of this invention there is provided a nucleotide sequence for use in treating Alzheimer's Disease (AD).

In a preferred embodiment of the invention the nucleotide sequence may be a shRNA, further preferably at least one of shRNA1 and shRNA7 having sequence listing as set forth in SEQ ID NO: 1 and 2, respectively. There is provided for the nucleotide sequence to be used together with an anti-laminin specific receptor antibody, preferably an anti-LRP/LR specific antibody, further preferably IgG1-iS18.

According to an eleventh aspect of this invention there is provided a method of treating Alzheimer's Disease (AD) comprising administering an anti-laminin specific receptor antibody, preferably an anti-37 kDa/67 kDa laminin receptor (LRP/LR) specific antibody, further preferably the anti-LRP/LR specific antibody may be IgG1-iS18 to a human or animal in need thereof.

According to a twelfth aspect of this invention there is provided a method of treating Alzheimer's Disease (AD) comprising administering a nucleotide sequence, preferably shRNA, further preferably at least one of shRNA1 and shRNA7 having sequence listing as set forth in SEQ ID NO: 1 and 2, respectively, to a human or animal in need thereof. The method may further include administering an anti-laminin specific receptor antibody, preferably an anti-LRP/LR specific antibody, further preferably IgG1-iS18, to the human or animal in need thereof.

BRIEF DESCRIPTION OF THE DRAWINGS

The invention is now described, by way of example only, with reference to the accompanying diagrammatic drawings, in which

FIG. 1aa shows black and white line drawings of FIG. 1a;

FIG. 1bb shows black and white line drawings of FIG. 1b;

FIG. 6a (ii) shows an immunoblot employed to validate the position of LRP::FLAG (~38 kDa);

FIG. 6b shows cellular viability of HEK293 cells, as determined by (3-(4,5-dimethylthiazol-2-yl)-2,5-diphenyltetrazolium bromide (MTT) (1 mg/ml) assay, post exogenous treatment with synthetic Aβ$_{42}$ and upon co-incubation with anti-LRP/LR IgG1-iS18 or IgG1-HD37 (negative control);

FIG. 6c shows cellular viability of SH-SY5Y cells;

FIG. 6d shows cellular viability of N2a cells;

FIG. 6e shows cellular proliferation of N2a cells as determined by colorimetric 5-bromo-2'-deoxyuridine (BrdU) non-isotopic immunoassay (Calbiochem®), allowing 4 h for BrdU incorporation into cultured cells.

DETAILED DESCRIPTION OF THE DRAWINGS

Figure 1A:
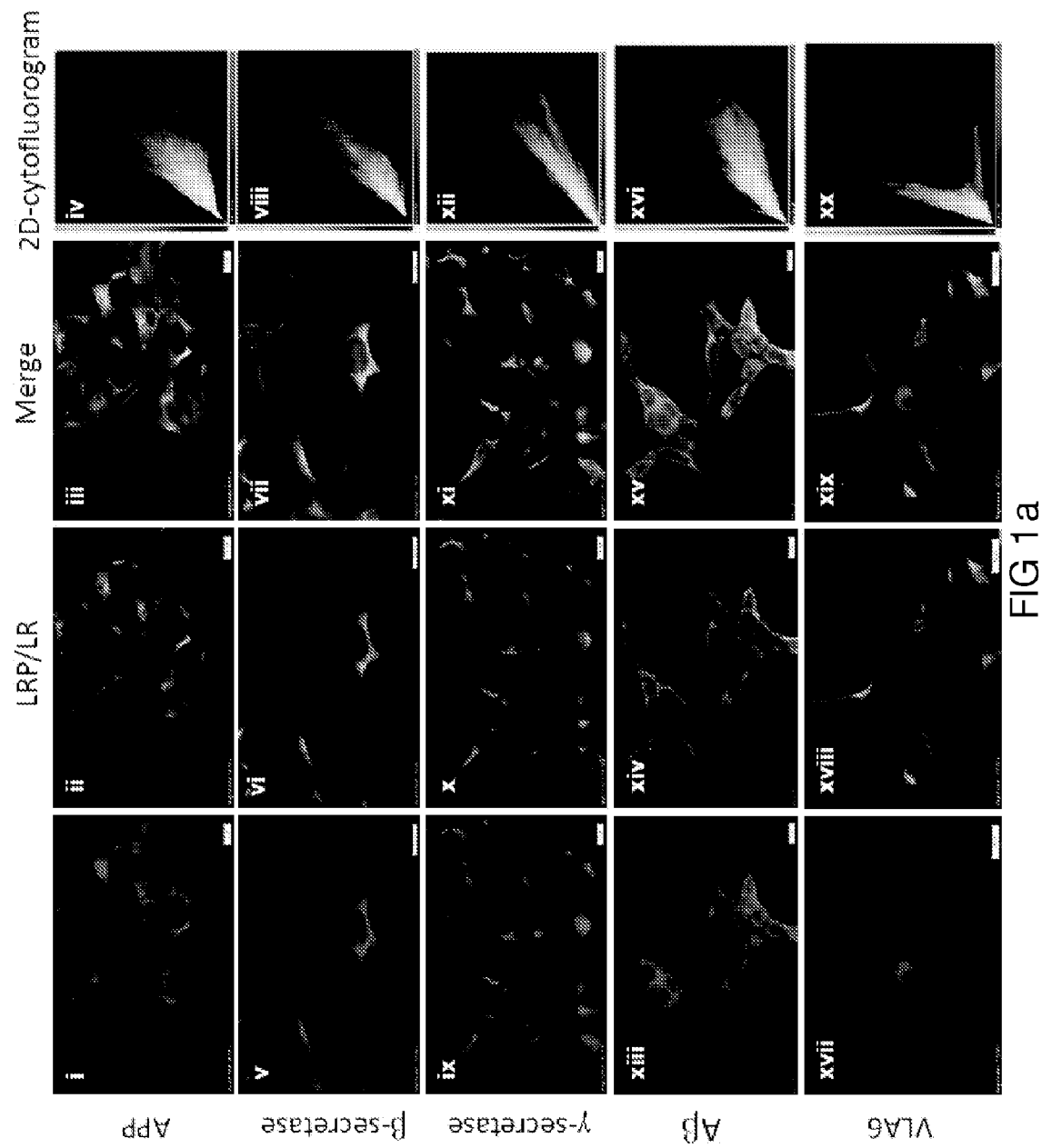
FIG. 1a shows co-localisation of 37 kDa/67 kDa laminin receptor (LRP/LR) with the Alzheimer's Disease (AD) relevant proteins amyloid precursor protein (APP), beta (β) and gamma (γ) secretases and amyloid beta peptide (Aβ), on the surface of human embryonic kidney cells (HEK293) cells via immunofluorescence microscopy.
Figure 1A:
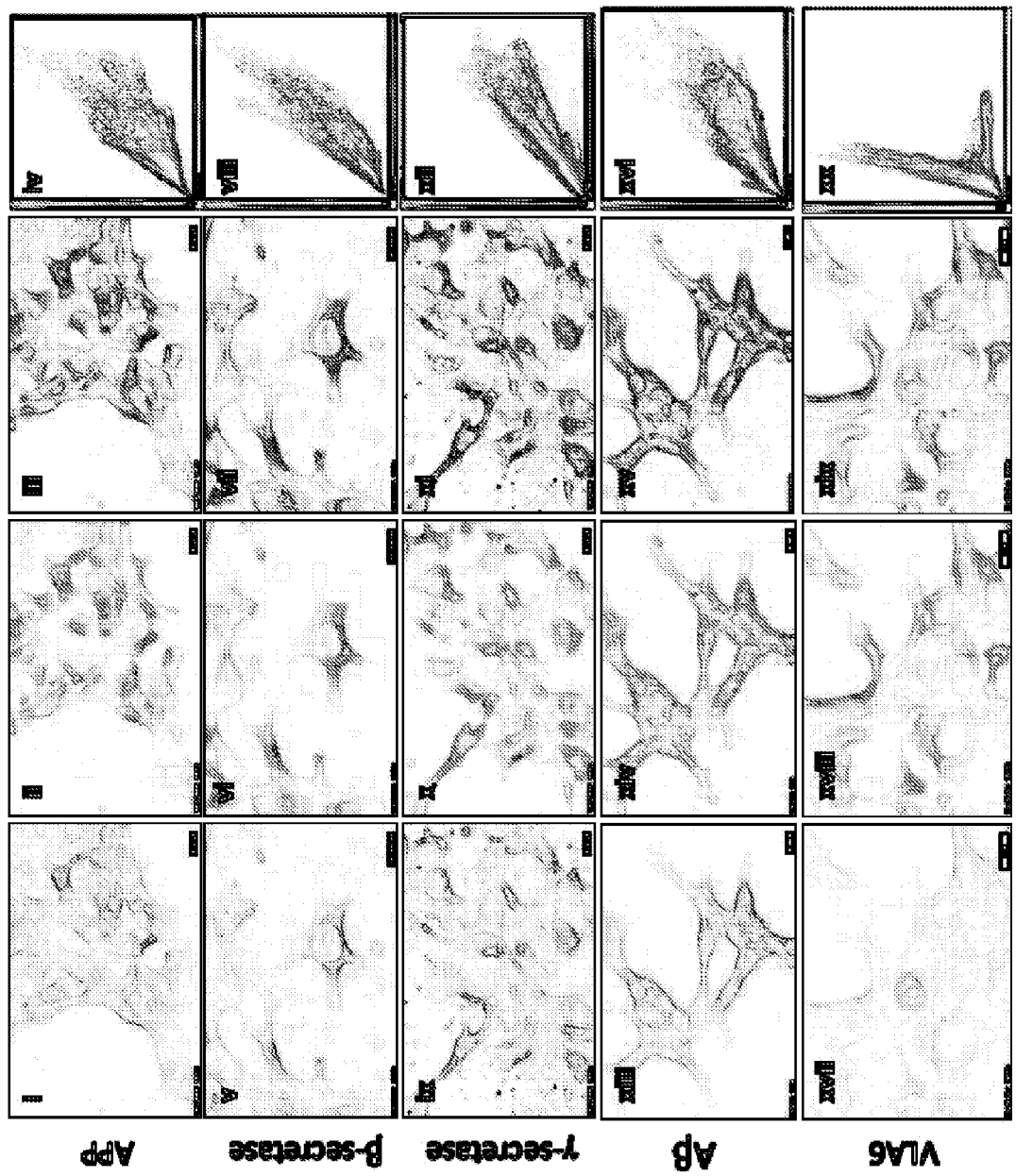

According to a first aspect of this invention there is provided a method for reducing concentration of at least one Alzheimer's Disease (AD) relevant protein selected from the group including, but not limited to, amyloid precursor protein (APP), beta (β) and gamma (γ) secretases and amyloid beta peptide (Aβ), the method comprising contacting a cell surface protein, preferably an extracellular matrix glycoprotein, with a cell surface protein specific antibody, preferably a monoclonal antibody, or any fragment of the aforementioned, such that binding occurs between a surface epitope of the cell surface protein and the cell surface protein specific antibody causing a decrease in the concentration of the at least one AD relevant proteins.

The reduction in concentration of the at least one AD relevant protein is a reduction relative to the amount of AD relevant proteins in a normal healthy human or animal, or relative to a human or animal suffering from AD.

It is to be understood that the binding between the surface epitope of the cell surface protein and the cell surface protein specific antibody at least hinders, preferably prevents, binding of at least one of the AD relevant proteins to the cell surface protein.

The cell surface protein may be a laminin receptor protein. However, in a preferred embodiment of the invention the laminin receptor is 37 kDa/67 kDa laminin receptor (LRP/LR) of a human and/or animal. LRP/LR is also known as LAMR, RPSA and p40. The cell surface protein may also be a protein showing at least 80% or greater homology to the laminin receptor protein, preferably showing at least 80% or greater homology to LRP/LR.

In the examples illustrated and/or exemplified below the AD relevant protein whose concentration is reduced via the method of this invention is Aβ. The reduced amount of Aβ causes reduced intracellular neurofibrillary tangle formation and/or reduced extracellular Aβ plaque deposition in human and/or animal cells, preferably neuronal cells, therein treating and/or preventing AD. When exercising this method of reducing Aβ concentration in an effort to treat and/or prevent AD, the contacting typically takes place in vivo.

The cell surface protein specific antibody may be any antibody, or fragment thereof, raised against the cell surface protein. Typically, the antibody is raised against LRP/LR or against a protein having 80% or greater homology with LRP/LR. The antibody, or fragment thereof, may be a F(ab')2 fragment, a Fab fragment scFv, a bi-specific scFv, a tri-specific scFv, a single chain or tandem diabody, a single domain antibody (dAb), a minibody or a molecular recognition unit (MRU). Furthermore, the antibody, or fragment thereof, may be monovalent, bivalent or multivalent. The antibody, or fragment thereof, may additionally comprise at least one further antigen-interaction site and/or at least one further effector domain. Preferably, the antibody or fragment thereof an anti-laminin receptor specific antibody, further preferably anti-LRP/LR specific antibody, still further preferably IgG1-iS18.

The cell surface protein and/or the cell surface protein specific antibody is typically a human or animal cell surface protein and/or cell surface protein specific antibody. The cell surface protein may be located on murine neuronal cells (N2a), human neuronal cells (SH-SY5Y), baby hamster kidney cells (BHK) and human embryonic kidney cells (HEK293 and/or HEK 293 FT).

In a preferred embodiment of the invention, the method for reducing concentration of at least one AD relevant protein comprises contacting LRP/LR with IgG1-iS18, or any fragment thereof, such that binding occurs between LRP/LR and IgG1-iS18, or any fragment thereof, causing a decrease in the concentration of Aβ. From a practical point of view, when exercising this method of reducing Aβ concentration in an effort to treat and/or prevent AD, the antibody (typically IgG1-iS18, or any fragment thereof) is formulated into a pharmaceutical composition and further formulated into a pharmaceutical dosage form to be administered to a human or animal in need of treatment. The pharmaceutical composition may include excipients. The dosage form may be formulated to deliver the pharmaceutical composition via oral and/or parenteral means.

According to a second aspect of this invention there is provided a method for reducing Aβ shedding caused by the proteolytic cleavage of APP by beta (β) and/or gamma (γ) secretases, the method comprising contacting the cell surface protein described above, with the cell surface protein specific antibody described above, such that binding occurs between a surface epitope of the cell surface protein and the cell surface protein specific antibody therein hindering the proteolytic cleavage of APP by beta (β) and/or gamma (γ) secretases.

The reduction in Aβ shedding may be a reduction relative to Aβ shedding in a normal healthy human or animal, or it may be a reduction relative to Aβ shedding in a human or animal suffering from AD.

It is to be understood that the binding between the surface epitope of the cell surface protein and the cell surface protein specific antibody at least hinders, preferably prevents, binding of at least one of the AD relevant proteins APP, beta (β) and gamma (γ) secretases and Aβ to the cell surface protein. It is further to be understood that it is this binding that causes a reduction in Aβ shedding.

As mentioned in the first aspect of the invention, in a preferred embodiment of the invention the cell surface protein is a laminin receptor, preferably the laminin receptor is LRP/LR of a human and/or animal. The cell surface protein may also be a protein showing at least 80% or greater homology to the laminin receptor protein, preferably showing at least 80% or greater homology to LRP/LR.

The cell surface protein specific antibody may be any antibody, or fragment thereof, raised against the cell surface protein. In a preferred embodiment the antibody is raised against LRP/LR or against a protein having 80% or greater homology with LRP/LR. The antibody, or fragment thereof, may be a F(ab')2 fragment, a Fab fragment scFv, a bi-specific scFv, a tri-specific scFv, a single chain or tandem diabody, a single domain antibody (dAb), a minibody or a molecular recognition unit (MRU). Furthermore, the antibody, or fragment thereof, may be monovalent, bivalent or multivalent. The antibody, or fragment thereof, may additionally comprise at least one further antigen-interaction site and/or at least one further effector domain.

In a preferred embodiment of the invention, the antibody or fragment thereof may be an anti-laminin receptor specific antibody, preferably an anti-LRP/LR specific antibody, further preferably IgG1-iS18.

In a preferred embodiment of the invention the cell surface protein and/or the cell surface protein specific antibody is a human or animal cell surface protein and/or cell surface protein specific antibody. The cell surface protein may be located on murine neuronal cells (N2a), human neuronal cells (SH-SY5Y), baby hamster kidney cells (BHK) and human embryonic kidney cells (HEK293 and/or HEK 293 FT).

In a preferred embodiment of the invention, the method for reducing Aβ shedding caused by the proteolytic cleavage of APP by beta (β) and gamma (γ) secretases, the method comprises contacting LRP/LR with IgG1-iS18, or any fragment thereof, such that binding occurs between LRP/LR and IgG1-iS18, or any fragment thereof, causing a reduction in Aβ shedding. As described in the first aspect of the invention above, the IgG1-iS18 is typically formulated into a pharmaceutical composition which is formulated into a pharmaceutical dosage form which is administered to a human or animal in need of AD treatment.

According to a third aspect of this invention there is provided a method for reducing concentration of at least one AD relevant protein selected from the group including, but not limited to, APP, beta (β) and gamma (γ) secretases and Aβ, the method comprising contacting a cell surface protein, preferably an extracellular matrix glycoprotein, with a nucleotide sequence, preferably an RNA sequence, further preferably a short hairpin RNA (shRNA) sequence or a short interfering RNA (siRNA) sequence or a micro RNA (miRNA) sequence, such that binding occurs between mRNA of the cell surface protein and the nucleotide sequence causing a downregulation of the cell surface protein which in turn causes a decrease in the concentration of the at last one AD relevant proteins.

The reduction in concentration of the at least one AD relevant protein is a reduction relative to the amount of AD relevant proteins in a normal healthy human or animal, or relative to a human or animal suffering from AD.

The cell surface protein may be a laminin receptor protein and preferably LRP/LR as described above in the first and second aspects of the invention. Preferably, when binding between the nucleotide sequence and the mRNA occurs, such binding is between the nucleotide sequence and LRP mRNA.

In a preferred embodiment of the invention the AD relevant protein whose concentration is reduced via the method of this invention is Aβ as described above.

The nucleotide sequence is preferably shRNA, further preferably at least one of shRNA1 and shRNA7 having sequence listing as set forth in SEQ ID NO: 1 and 2, respectively.

In a preferred embodiment of the invention, the method for reducing concentration of at least one AD relevant protein selected from the group including, but not limited to, APP, beta (β) and gamma (γ) secretases and Aβ, the method comprises contacting LRP/LR with shRNA1 and/or shRNA7 having sequence listing as set forth in SEQ ID NO: 1 and 2, respectively, such that binding occurs between LRP mRNA and shRNA1 and/or shRNA7 causing a decrease in the concentration of Aβ.

According to a fourth aspect of this invention there is provided a method for reducing Aβ shedding caused by the proteolytic cleavage of amyloid precursor protein (APP) by beta (β) and gamma (γ) secretases, the method comprising contacting a cell surface protein, preferably an extracellular matrix glycoprotein, with a nucleotide sequence, preferably an RNA sequence, further preferably a short hairpin RNA (shRNA) sequence or a short interfering RNA (siRNA) sequence or a micro RNA (miRNA) sequence, such that binding occurs between mRNA of the cell surface protein and the nucleotide sequence causing a downregulation of the cell surface protein which in turn causes a decrease in the proteolytic cleavage of APP by beta (β) and gamma (γ) secretases.

The cell surface protein may be a laminin receptor protein and preferably LRP/LR as described above in the first and second aspects of the invention. Preferably, when binding between the nucleotide sequence and the mRNA occurs, such binding is between the nucleotide sequence and LRP mRNA.

The reduction in Aβ shedding may be a reduction relative to Aβ shedding in a normal healthy human or animal, or it may be a reduction relative to Aβ shedding in a human or animal suffering from AD.

The nucleotide sequence is preferably a shRNA, further preferably at least one of shRNA1 and shRNA7 having sequence listing as set forth in SEQ ID NO: 1 and 2, respectively.

In a preferred embodiment of the invention, the method for reducing Aβ shedding caused by the proteolytic cleavage of APP by beta (β) and gamma (γ) secretases, the method comprises contacting LRP/LR with shRNA1 and/or shRNA7 having sequence listing as set forth in SEQ ID NO: 1 and 2 respectively, such that binding occurs between LRP mRNA and shRNA1 and/or shRNA7 causing a reduction in LRP/LR cell surface levels and hence a reduction in Aβ shedding.

According to a fifth aspect of this invention there is provided a method for reducing concentration of at least one AD relevant protein selected from the group including, but not limited to, APP, beta (β) and gamma (γ) secretases and Aβ, the method comprising contacting a cell surface protein of the first aspect of the invention with the antibody the first aspect of the invention and the nucleotide sequence of the third aspect of the invention. Essentially, the LRP/LR is downregulated by the shRNAs (either shRNA1 or 7 or both) and is substantially blocked by the anti-LRP/LR specific antibody, in so doing, further reducing the concentration of Aβ.

According to a sixth aspect of this invention there is provided a method for reducing Aβ shedding caused by the proteolytic cleavage of APP by beta (β) and gamma (γ) secretases, the method comprising the method comprising contacting a cell surface protein of the second aspect of the invention with the antibody the second aspect of the invention and the nucleotide sequence of the fourth aspect of the invention. Essentially, the LRP/LR is downregulated by the shRNAs (either shRNA 1 or 7 or both) and is substantially blocked by the anti-LRP/LR specific antibody, in so doing, further reducing Aβ shedding.

According to a seventh aspect of this invention there is provided for use of an anti-laminin receptor specific antibody in the manufacture of a pharmaceutical composition to treat AD. Typically, the anti-laminin receptor specific antibody is IgG1-iS18.

According to an eighth aspect of this invention there is provided an anti-laminin receptor specific antibody for use in treating AD. Typically, the anti-laminin receptor specific antibody is IgG1-iS18.

According to a ninth aspect of this invention there is provided for use of a nucleotide sequence in the manufacture of a pharmaceutical composition to treat AD. Typically, the nucleotide sequence may be RNA, preferably a shRNA, further preferably at least one of shRNA1 and shRNA7 having sequence listing as set forth in SEQ ID NO: 1 and 2, respectively. The use may further include an anti-laminin receptor specific antibody described above.

According to a tenth aspect of this invention there is provided a nucleotide sequence for use in treating AD. Typically, the nucleotide sequence may be RNA, preferably a shRNA, further preferably at least one of shRNA1 and shRNA7 having sequence listing as set forth in SEQ ID NO: 1 and 2, respectively. There is provided for the nucleotide sequence to be used together with an anti-laminin receptor specific antibody described above for use in treating AD.

According to an eleventh aspect of this invention there is provided a method of treating AD comprising administering an anti-laminin receptor specific antibody, preferably an anti-LRP/LR specific antibody, further preferably IgG1-iS18 to a human or animal in need thereof.

According to a twelfth aspect of this invention there is provided a method of treating AD comprising administering a nucleotide sequence, preferably a RNA sequence, further preferably shRNA, further preferably at least one of shRNA1 and shRNA7 having sequence listing as set forth in SEQ ID NO: 1 and 2, respectively, to a human or animal in need thereof. The method may further include administering an anti-laminin receptor specific antibody, preferably an anti-LRP/LR specific antibody, further preferably IgG1-iS18 to the human or animal.

EXAMPLES

A representative example of the invention is described and/or illustrated and/or exemplified below and should not be viewed as limiting to the scope of the invention. The sequence listing attached hereto is incorporated by reference.

In the examples of the invention illustrated and exemplified below, it is shown that 37 kDa/67 kDa laminin receptor (LRP/LR) is associated with the Alzheimer's Disease (AD) relevant proteins amaloid precursor protein (APP), β- and γ-secretase as well as amaloid beta peptide (Aβ). It was found that Aβ binds to LRP/LR and this interaction may contribute to Aβ-induced cytotoxicity. Furthermore, antibody blockage (or substantial blockage) and shRNA downregulation of LRP/LR was shown to reduce Aβ shedding, due to impediment of P-secretase activity, rather than alteration of APP, P— and γ-secretase levels. These findings indicate that LRP/LR may be implicated in AD pathogenesis and could lead to novel therapeutic interventions for use in modulating LRP/LR and/or modulating the concentration of AD relevant proteins APP, P— and γ-secretases and Aβ in a human or animal in the treatment of AD.

The extracellular matrix glycoprotein, laminin, exhibits an Aβ binding site, namely the IKAV peptide sequence located on the alpha (α) chain of the tri-peptide[15]. However, the association between laminin and Aβ is reported to promote neurite outgrowth[16] and inhibit fibrillogenesis[15] and thereby thwart Aβ pathogenesis. Prior research does not suggest LRP/LR functioning being important in the determining concentrations of the abovementioned AD relevant proteins, specifically Aβ, nor does the prior art suggest that LRP/LR could play any role in impeding β-secretase activity.

LRP/LR (also known as LAMR, RPSA and p40) is a multifunctional protein located within the cholesterol-rich lipid raft domains of the plasma membrane, in the cytoplasm as well as in the nucleus[17]. Associations between LRP/LR and a multitude of extracellular (laminin and elastin) and intracellular (cytoskeletal proteins, histones, heparan sulfate proteoglycans (HSPGs)) components have been described, and are of physiological significance[18].

The experimental protocols described hereunder show a nexus between LRP/LR and the amyloidgenic pathway in AD, more specifically a nexus between LRP/LR and Aβ shedding into the extracellular space.

To explore the above mentioned nexus indirect immunofluorescence microscopy was employed to assess the cellular distribution of AD relevant proteins, namely the APP, β- and γ-secretases and Aβ. LRP/LR was shown to co-localise with APP (FIG. 1a, i-iv), β-secretase (FIG. 1a, v-viii), γ-secretase (FIG. 1a, ix-xii) and Aβ (FIG. 1a, xiii-xvi) on the surface of non-permeabilised human embryonic kidney cells (HEK293). An alternative laminin binding receptor, Very Late Antigen 6 (VLA6), was employed as a negative control (FIG. 1a, xvii-xx). Analogous results were obtained for murine neuroblastoma (N2a) cells (FIG. 1b).

In general, FIG. 1a shows co-localisation of LRP/LR with the AD relevant proteins APP, β-secretase, γ-secretase and Aβ on the surface of human embryonic kidney cells (HEK293 and/or HEK 293 FT) cells. FIG. 1a shows cell surface receptors on HEK293 cells having been indirectly immunolabelled to allow for detection using the Olympus IX71 Immunofluorescence Microscope and Analysis Get It Research Software. In particular, FIG. 1a shows (i) APP (detected by anti-APP (rabbit polyclonal IgG) (Abeam), (v), β-secretase (detected using anti-BACE (M-83) (rabbit polyclonal IgG) (Santa Cruz Biotechnology)), (ix), γ-secretase (detected by anti-PEN-2 (FL-101) (rabbit polyclonal IgG) (Santa Cruz Biotechnology)), (xii), Aβ (detected using anti-β-amyloid (22-35) (Sigma)) and (xvii), VLA6 (detected by anti-very late antigen-6 (VLA6) CD49-f (rabbit monoclonal IgG) (Immunotech) were indirectly labelled with Alexaflour 633, while an anti-human FITC coupled antibody (Cell Lab) was used to label LRP/LR (ii, vi, x, xiv, xviii).

The merges between LRP/LR and AD relevant proteins are shown (iii, vii, xi, xv, xix) in FIG. 1a and the corresponding 2D-cytofluorograms (acquired using CellSens Software) have been included to confirm the degree of co-localisation (iv, viii, xii, xvi, xx).

Figure 1B:
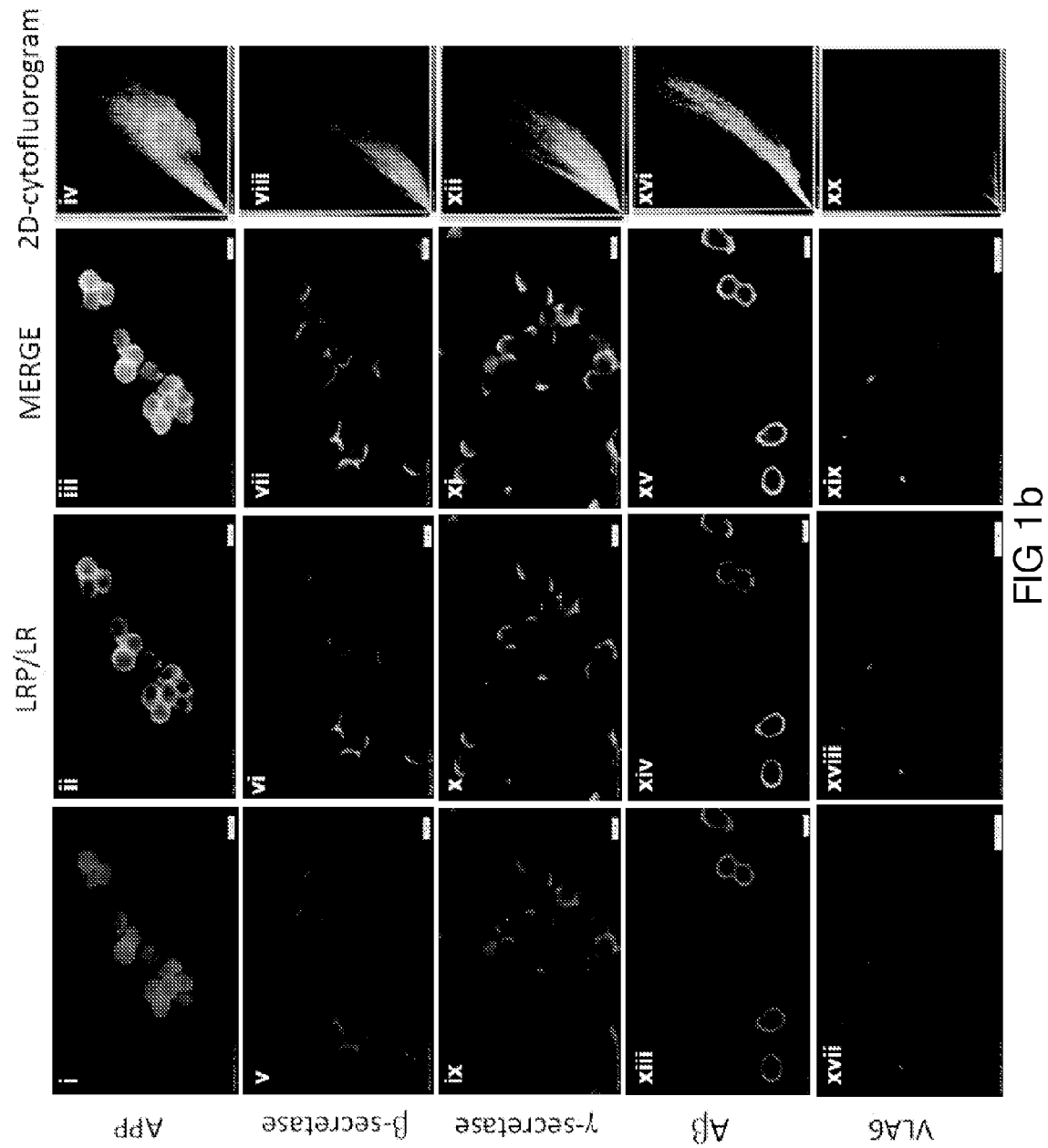
FIG. 1b shows co-localisation of LRP/LR with the AD relevant proteins APP, beta (β) and gamma (γ) secretases and Aβ, on the surface of murine neuroblastoma (N2a) cells via immunofluorescence microscopy.
Figure 1B:
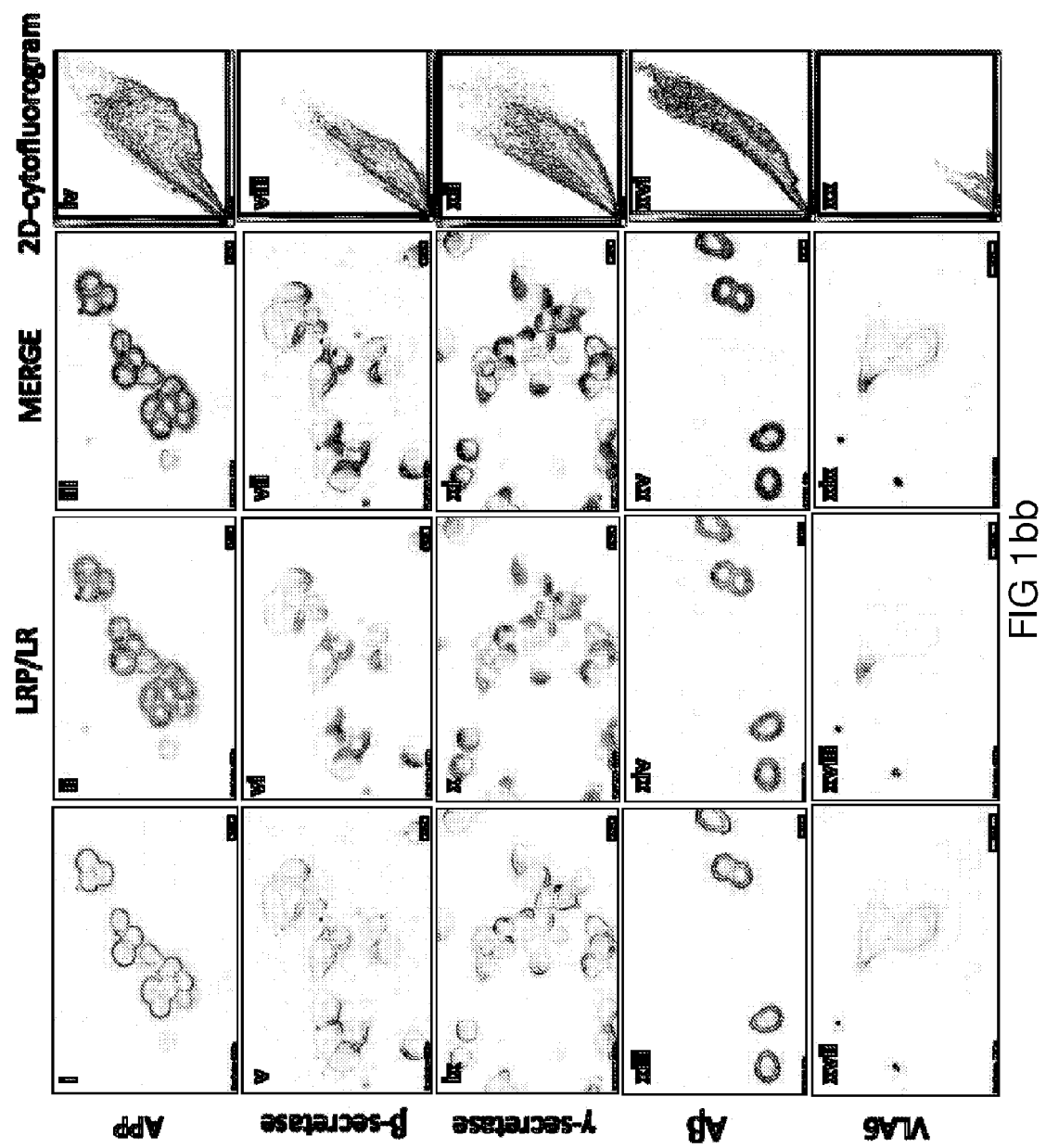

FIG. 1b shows the same as FIG. 1a above, but as seen on the surface of N2a cells. Scale bars on the figures are 10 µm.

The proximity of the AD relevant proteins on the cell surface thereby suggested that an association/interaction between LRP/LR and AD relevant proteins is feasible and that the j receptor may indeed be implicated in AD pathogenesis. 2D-cytofluorograms (FIGS. 1a and b, iv, viii, xii, xvi) show the joint distribution of the red and green fluorescence, with a diagonal indicating co-localisation between the cell surface proteins of interest. FIG. 1aa and 1bb show a black and white reproducible version of FIGS. 1a and 1b, where a diagonal again indicates co-localisation between the cell surface proteins of interest. Pearson's Correlation co-efficients for co-localisation were employed to further confirm the observed results as shown in Table 1 below.

Table 1 shows Pearson's Correlation Co-efficient for Co-localisation between LRP/LR and AD relevant proteins

|  | human embryonic kidney cells (HEK293) | Murine neuronal cells (N2a) |
| --- | --- | --- |
| LRP/LR + APP | 0.862 | 0.948 |
| LRP/LR + Aβ | 0.926 | 0.969 |
| LRP/LR + β-secretase | 0.915 | 0.900 |
| LRP/LR + γ-secretase | 0.938 | 0.914 |
| LRP/LR + VLA6 | 0.583 | 0.563 |

The Pearson's Correlation co-efficient was employed to determine the degree of co-localisation between proteins of interest, where 1 indicates complete co-localisation and 0 is indicative of no co-localisation between proteins of interest. The co-efficient was calculated for LRP/LR and AD relevant proteins APP, Aβ, β- and γ-secretase respectively, as well as the negative control VLA6.

To investigate whether the LRP/LR is involved in the amyloidogenic pathway, and more specifically Aβ shedding into the extracellular space, cells were treated with the anti-LRP/LR specific antibody IgG1-iS18[21] and anti-cluster of differentiation (CD 19) antibody IgG1HD37[21] (negative control).

Figure 2A:
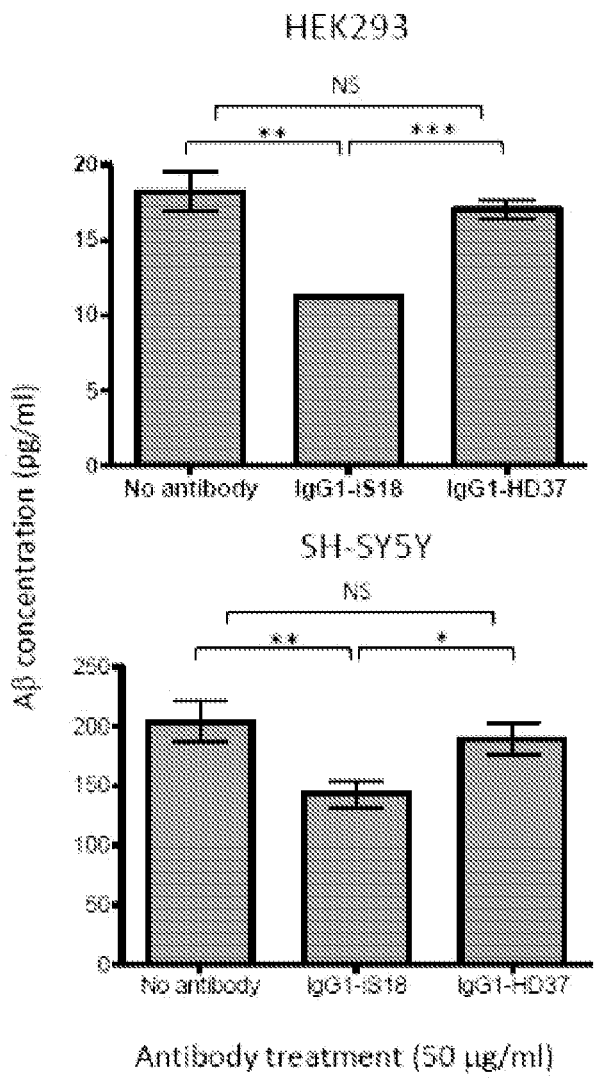
FIG. 2a shows Aβ concentrations in HEK293 and human neuronal cells (SH-SY5Y) cells after treatment with antibodies IgG1-iS18 and IgG1-HD37 as detected by an Aβ ELISA (Human Amyloid β(1–x) Assay Kit (IBL)) after 18 hours of antibody incubation.
Figure 2B:
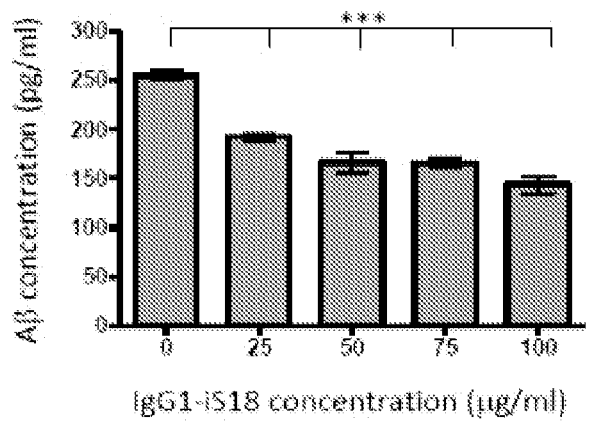
FIG. 2b shows Aβ concentrations after SH-SY5Y cells were treated with varying doses of IgG1-iS18 for 18 hours, as determined by an Aβ ELISA.

Essentially, cellular incubation with IgG1-iS18 resulted in a significant reduction (47.6% in human embryonic kidney cells (HEK293FT) and 28.5% in human neuronal cells (SH-SY5Y)) in Aβ concentration when compared to the no antibody control (FIG. 2a). To assess the optimal concentration of IgG1-iS18 for Aβ shedding impairment, dose dependency assays were conducted and a noteworthy reduction in Aβ concentration was observed for 25 µg/ml, 50 µg/ml, 75 µg/ml and 100 µg/ml (FIG. 2b). The distinction between 50 µg/ml-100 µg/ml was nominal and thus the of choice 50 µg/ml IgG1-iS18 for further experimental procedures was warranted.

In general, FIG. 2 shows the effects of IgG1-iS18 on Aβ concentration. FIG. 2a shows Aβ concentrations in HEK293 and SH-SY5Y cells after treatment with IgG1-iS18 and IgG1-HD37 as detected by an Aβ ELISA (Human Amyloid β(1-x) Assay Kit (IBL)) after 18 hours of antibody incubation. Data shown (mean±s.e.m) are representative of three independent experiments (performed in triplicate) per cell line. *p<0.05, p<0.01, *p<0.001, NS not significant; Student's t-test.

FIG. 2b shows Aβ concentrations after SH-SY5Y cells were treated with varying doses of IgG1-iS18 for 18 hours, as determined by an Aβ ELISA. Data shown (Mean±s.d.) comparing Aβ levels of untreated cells (0 µg/ml) and IgG1-iS18 treated cells (25-100 µg/ml), ***p<0.001; n=3; Student's t-test.

Figure 2C:
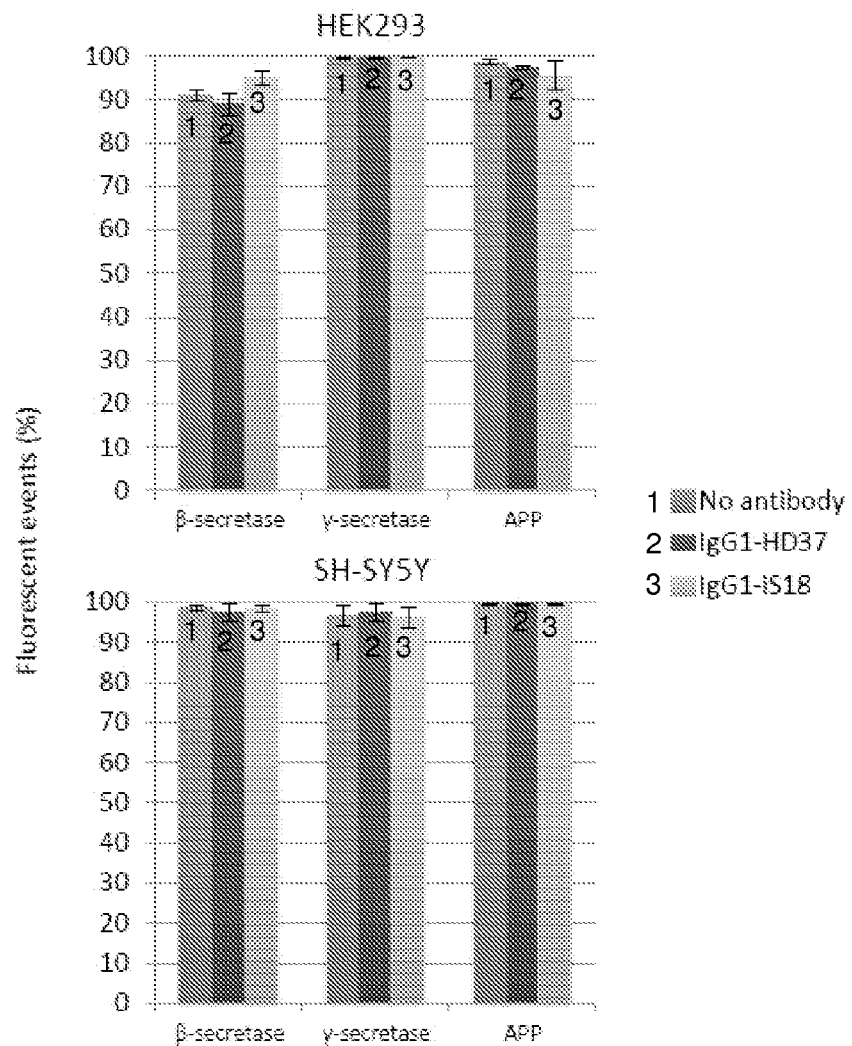
FIG. 2c shows flow cytometric analysis of APP, β-secretase and γ-secretase levels on the surface of human embryonic kidney cells (HEK293FT) and SH-SY5Y cells post treatment with IgG1-iS18.

FIG. 2c shows flow cytometric analysis of APP, β-secretase and γ-secretase levels on the surface of HEK293FT and SH-SY5Y cells post treatment with IgG1-iS18 (mean±s.d., NS not significant, n=3, Student's t-test).

Figure 2D:
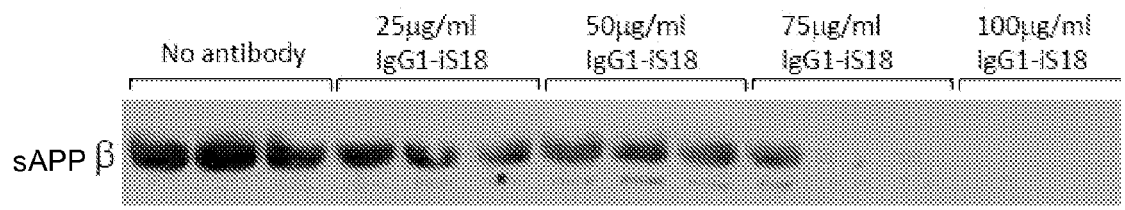
FIG. 2d shows a Western blot analysis depicting sAPPβ (SAPPβ is a shedded cleavage product of APP generated by the action of β-secretase) levels from cell culture medium after SH-SY5Y cells were treated with varying concentrations (0-100 µg/ml) of IgG1-iS18 for 18 hours.

FIG. 2d shows a Western blot analysis depicting sAPPβ (the shedded cleavage product after cleavage of APP by β-secretase) levels from cell culture medium after SH-SY5Y cells were treated with varying concentrations (0-100 µg/ml) of IgG1-iS18 for 18 hours. Western blot band intensities from three independent experiments were quantified using Quantity One 4.6 software.

Owing to the ability of IgG1-iS18 to decrease Aβ concentration, it is thought that LRP/LR mediates this process. To further confirm this role in the amyloidogenic pathway, RNA interference technology, specifically short hairpin RNA (shRNA) (see FIG. 3), was employed to downregulate LRP/LR expression as shown in FIG. 4.

Figure 3:
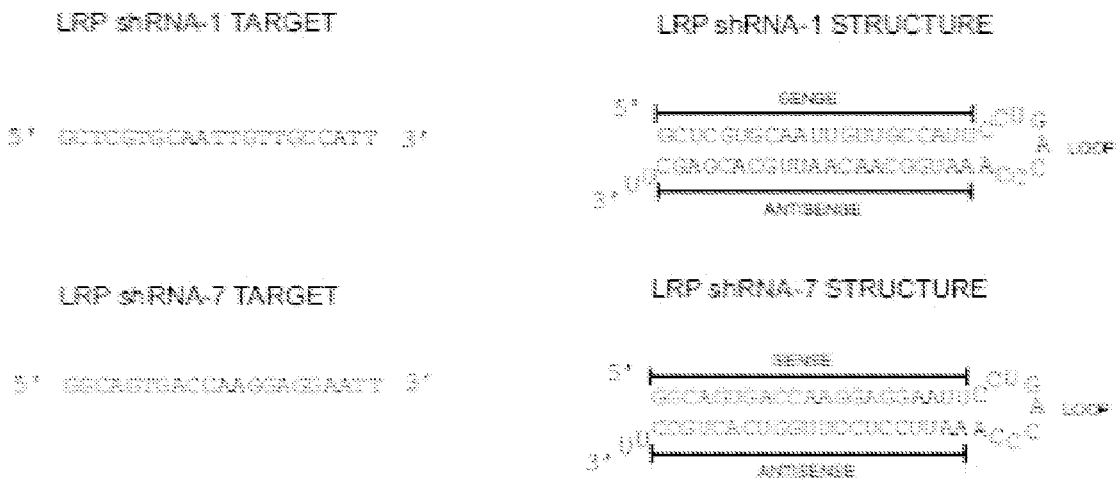
FIG. 3 shows LRP/LR target sequences and structure of short hairpin RNA1 (shRNA1) and short hairpin RNA7 (shRNA7)

FIG. 3 shows LRP/LR target sequences and structure of shRNA1 and shRNA7. It is to be understood that the references to thymine should are to be read as uracil since the nucleotide sequences are RNA. The sequence data for both shRNA1 and shRNA7 are attached hereto as SEQ ID NO: 1 and 2 respectively. The complete shRNA expression cassettes were designed with the guide strand on the 3'arm, a poly T termination signal, and to include a full HI RNA polymerase III promoter sequence. To prepare the shRNA cassettes, the HI RNA Pol III promoter was used as a template in a nested polymerase chain reaction (PCR), whereby the sequences corresponding to the shRNAs were incorporated into two reverse primers (one for the primary PCR and one for the secondary PCR). The same forward primer, which is complementary to the start of the HI promoter, was used in both. The PCR products coding for the shRNA expression constructs were sub-cloned into the pTZ57R/T vector (Fermentas). A scrambled shRNA (shRNAscr) that does not target any gene product was used as a negative control.

In general, FIG. 4 shows the effects of shRNA on downregulation of LRP/LR. FIG. 4a shows a Western Blot analysis of HEK293 cells that were transfected with LRP-specific shRNA1 and shRNA7 (as well as a scrambled control, shRNAscr). 72 hours post-transfection, cells were lysed and LRP levels assessed by Western blotting. β-actin was used as a loading control. Western blot band intensities from three independent experiments were quantified using Quantity One 4.6 Software.

Figure 4A:
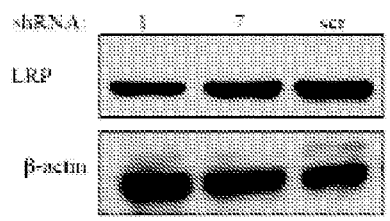
FIG. 4a shows a Western Blot analysis of HEK293 cells transfected with LRP-specific shRNA1 and shRNA7 (as well as a scrambled control, shRNAscr)
Figure 4B:
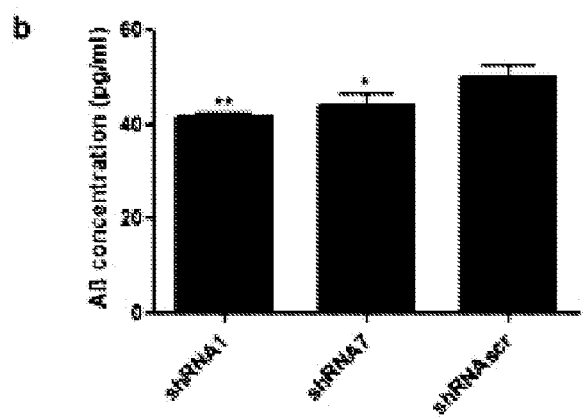
FIG. 4b shows the effects of shRNA on downregulation of LRP/LR wherein the Aβ concentration of the cell culture medium of shRNA-transfected HEK293 cells was analysed using an Aβ ELISA.

FIG. 4b shows the Aβ concentration of the cell culture medium of shRNA-transfected HEK293 cells analysed using an Aβ ELISA. Data shown (Mean±s.d.) compare Aβ levels of shRNA1 and shRNA7 to shRNAscr, *p<0.05, **p<0.01;

n=3; Student's t-test. Thus FIG. 4b shows the effects of shRNA on downregulation of LRP/LR.

Figure 4C:
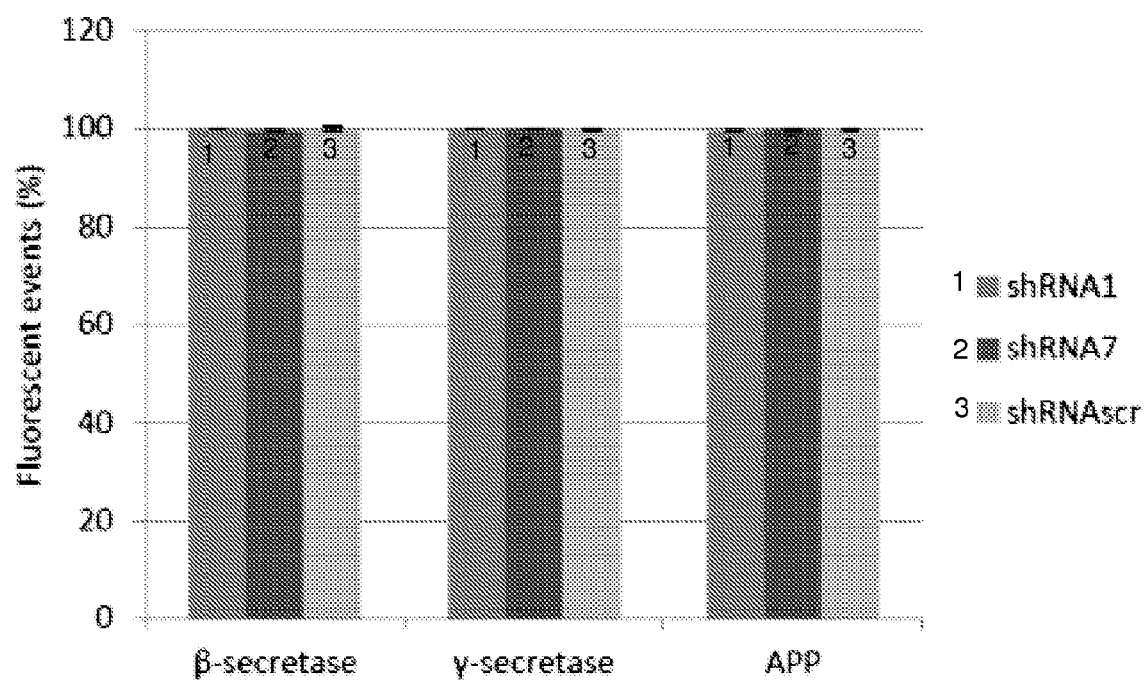
FIG. 4c shows flow cytometric analysis of APP, β-secretase and γ-secretase levels on the surface of shRNA-transfected HEK293 cells.

FIG. 4c shows flow cytometric analysis of APP, β-secretase and γ-secretase levels on the surface of shRNA-transfected HEK293 cells. Data shown (Mean±s.d.); n=3; Student's t-test.

Figure 4D:
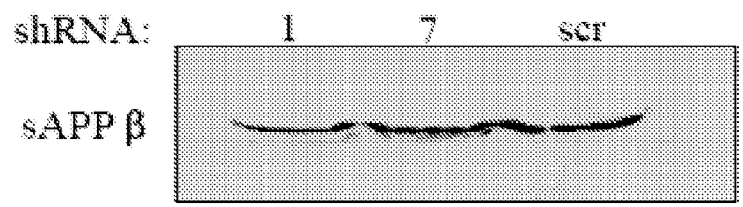
FIG. 4d shows sAPPβ levels in shRNA-transfected HEK293 cells were analysed by Western blotting.

FIG. 4d shows sAPPβ levels in shRNA-transfected HEK293 cells analysed by Western blotting.

Figure 4E:
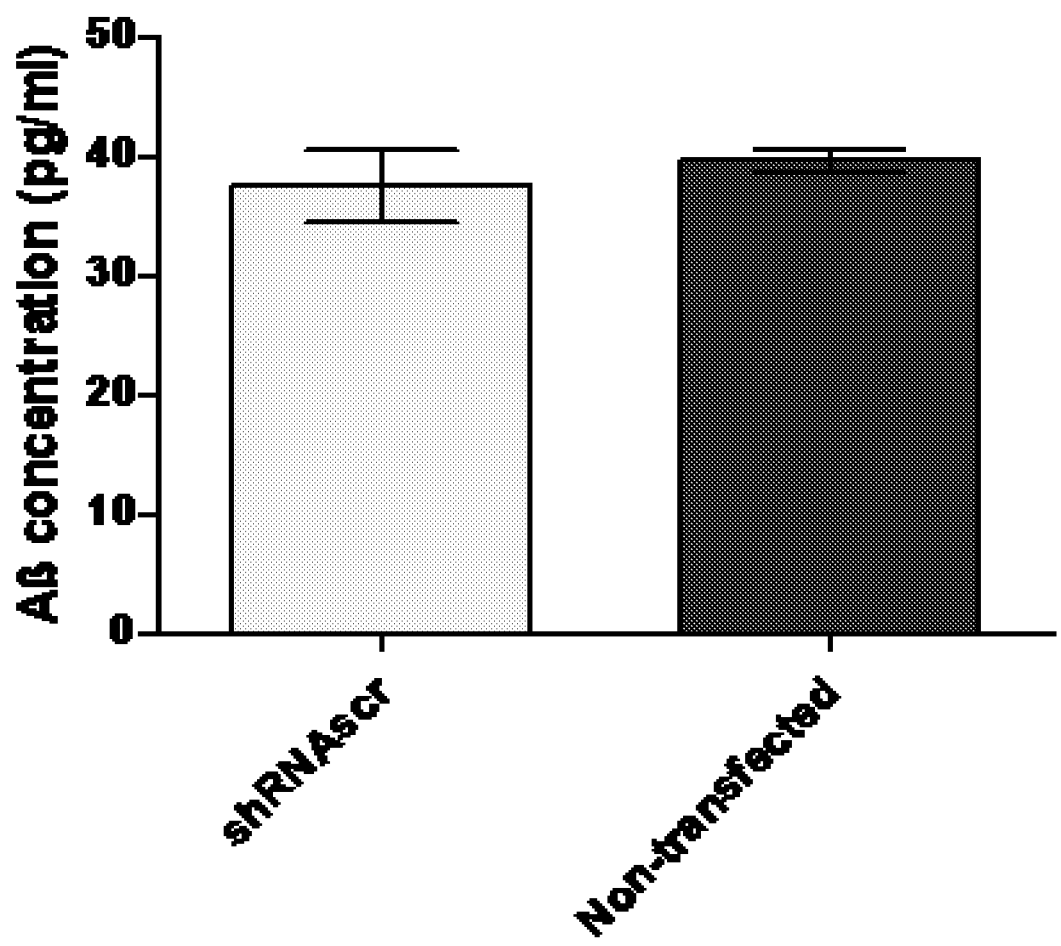
FIG. 4e shows Aβ concentration of the cell culture medium of shRNAscr-transfected and mock-transfected HEK293 cells.

These experiments, illustrated by FIGS. 4a-d, showed that shRNA1 and shRNA7 resulted in a significant 42.85% and 16.42% decrease in LRP/LR expression levels, respectively, compared to the scrambled control (shRNAscr) (FIG. 4e). This downregulation correlated to a significant 16.88% and 11.95% decrease in Aβ shedding in HEK293 cells (for shRNA1 and shRNA7 respectively) (FIG. 4b).

No significant difference was observed between mock-transfected and shRNAscr control transfected HEK293 cells (as can be seen in FIG. 4e). FIG. 4e shows Aβ concentration of the cell culture medium of shRNAscr-transfected and mock-transfected HEK293 cells. HEK293 cells were either transfected with the scrambled control (shRNAscr) or mock-transfected with no plasmid. 72 hours post transfection, the Aβ concentration of the cell culture medium was analysed using an Aβ ELISA. Data shown (Mean±s.d); n=3; Student's t-test; p0.05.

To investigate whether the receptor influences the amyloidogenic pathway through altering cell surface protein expression levels of APP, β-secretase and γ-secretase, flow cytometric analysis of the cell surface levels of APP, β-secretase and γ-secretase was performed post antibody (FIG. 2c) and shRNA treatment (FIG. 4c). Blockage and/or downregulation of LRP/LR did not significantly alter cell surface expression levels of the aforementioned proteins in comparison to controls as shown in FIG. 5. This suggests that the involvement of LRP/LR in the amyloidogenic process may be independent of gene expression modulation and possibly entails receptor interactions with the AD relevant proteins.

Figure 5A:
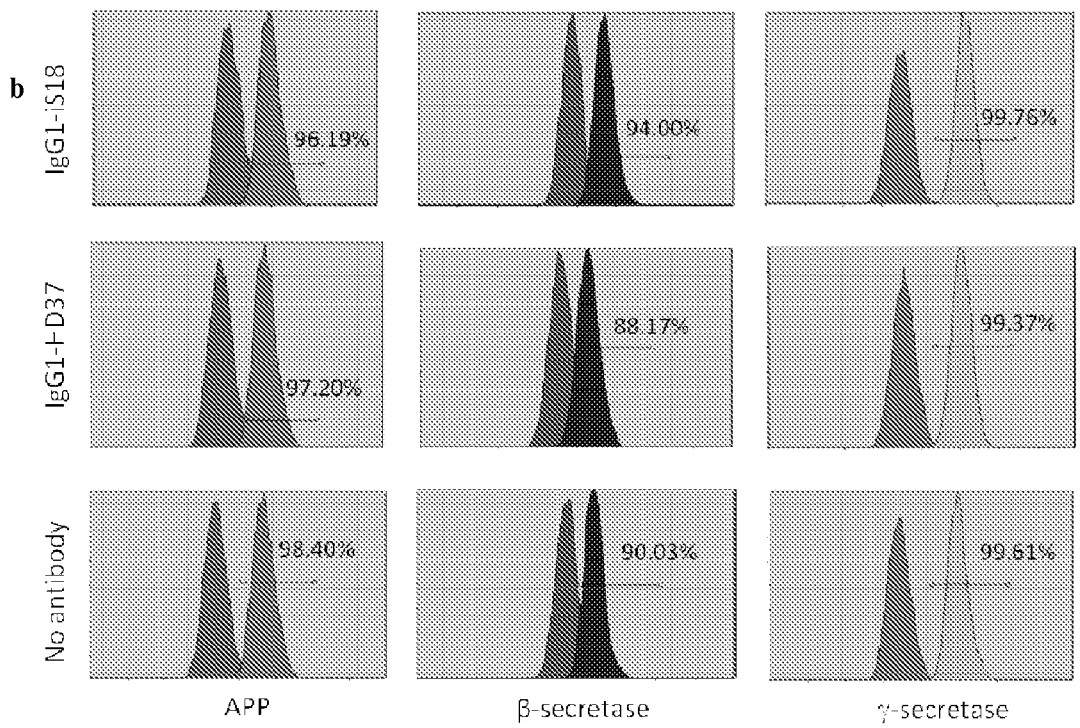
FIG. 5a shows flow cytometry histogram overlay plots for β-secretase, γ-secretase and APP after antibody treatment to HEK293 cells.

FIG. 5 shows flow cytometry histogram overlay plots for β-secretase, γ-secretase and APP after antibody or shRNA treatments. In particular, FIG. 5a shows flow cytometry histogram overlay plots after HEK293 cells were incubated with either 50 μg/ml IgG1-iS18, IgG1-HD37 or no antibody for 18 hours after which APP, β- and γ-secretase cell surface levels were ascertained by flow cytometry (Coulter EPICS® XL-MCL). β-secretase levels was detected using anti-BACE (M-83) (rabbit polyclonal IgG) (Santa Cruz Biotechnology) and goat anti-rabbit FITC secondary antibody (Cell labs), γ-secretase levels on the surface of the cells was detected by a primary antibody directed against the PEN-2 subunit of the γ-secretase complex (anti-PEN-2 (FL-101) (rabbit polyclonal IgG) (Santa Cruz Biotechnology)), and the corresponding goat anti-rabbit FITC secondary antibody. Cell surface APP levels were ascertained using an anti-APP (rabbit polyclonal IgG) (Abeam) and the corresponding goat anti-rabbit FITC secondary antibody. Images shown are averages of 3 independent experiments.

Figure 5B:
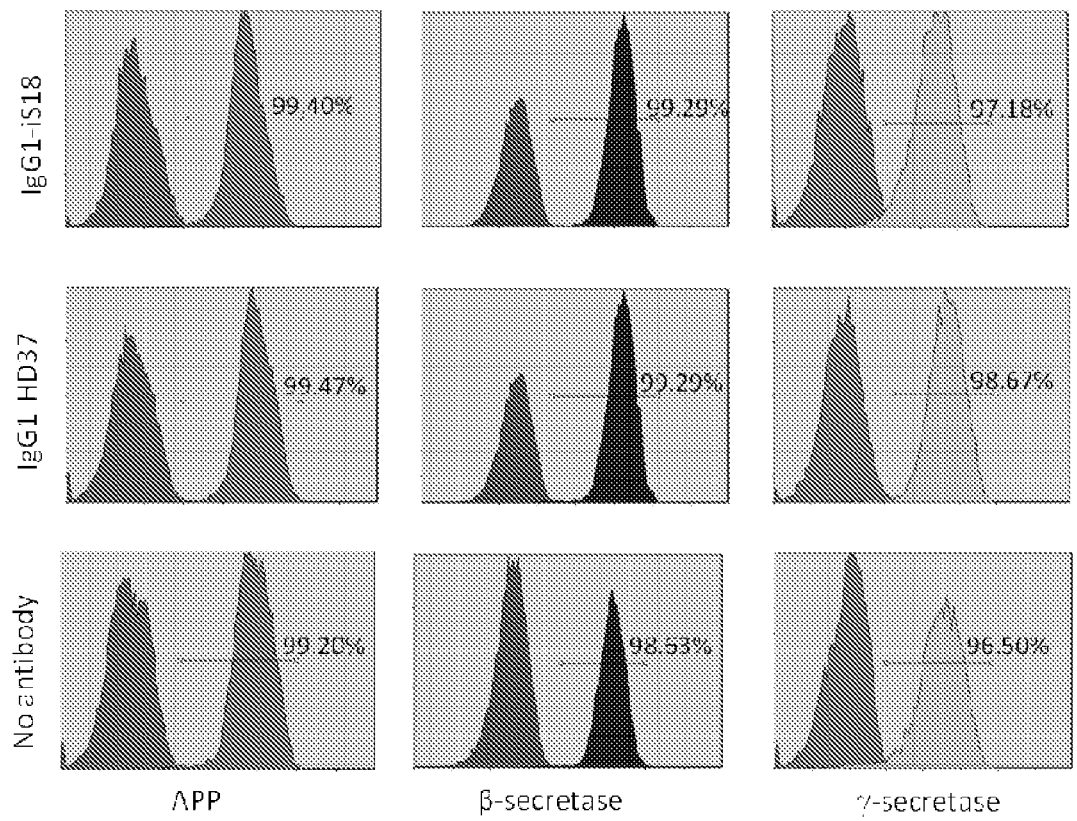
FIG. 5b shows flow cytometry histogram overlay plots for β-secretase, γ-secretase and APP after antibody treatment to SH-SY5Y cells.

FIG. 5b shows the same as above in FIG. 5a but with SH-SY5Y cells.

Figure 5C:
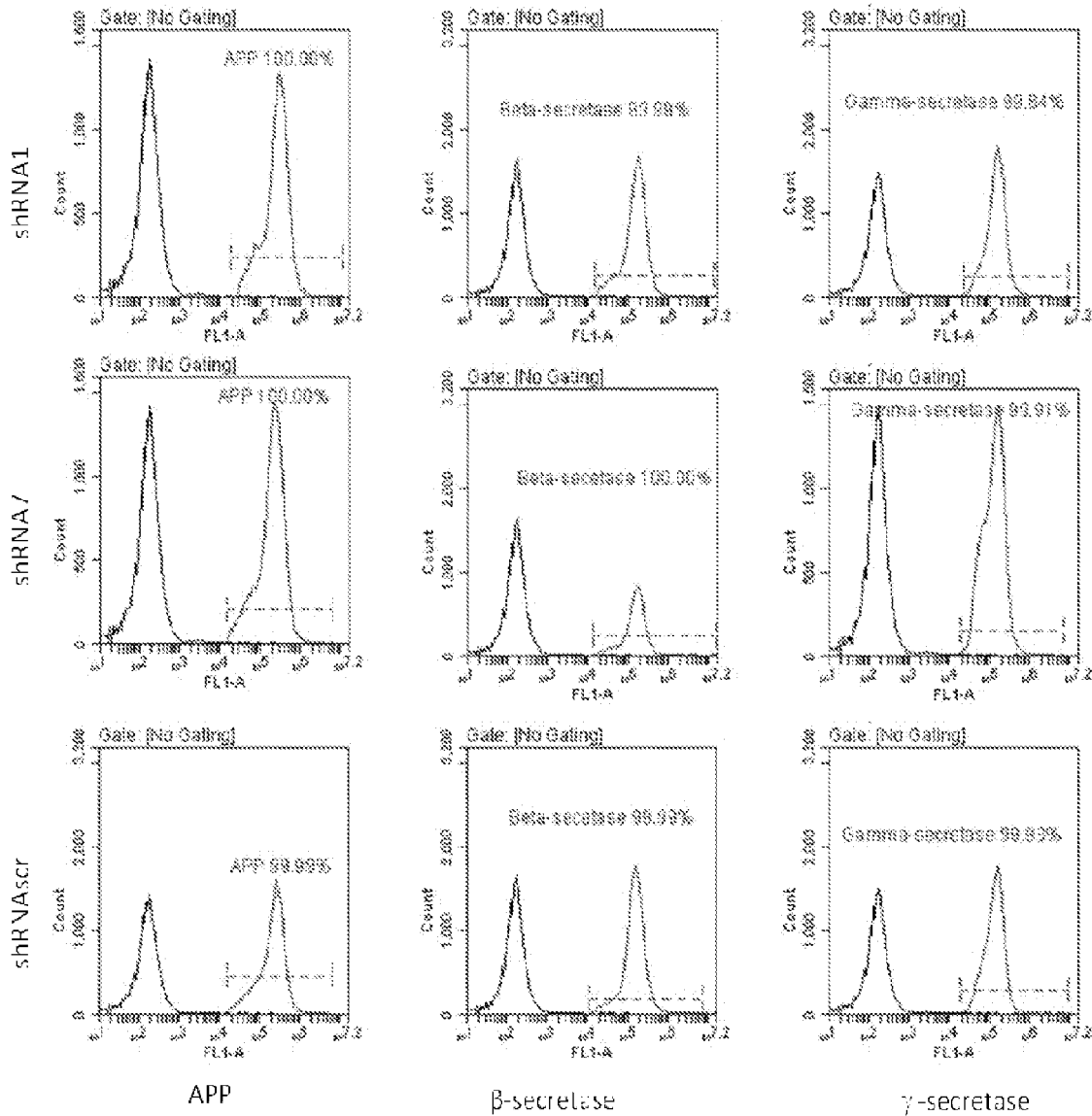
FIG. 5c shows flow cytometry histogram overlay plots for β-secretase, γ-secretase and APP after shRNA treatment to HEK293 cells were transfected with either shRNA1, shRNA7 or shRNAscr.

FIG. 5c shows flow cytometry histogram overlay plots after HEK293 cells having been transfected with either shRNA1, shRNA7 or shRNAscr. 72 hours post transfection, the cell surface levels of APP, β- and γ-secretase were ascertained by flow cytometry (BD Accuri C6) using the methodology described above.

The fact that blockage and/or downregulation of LRP/LR did not significantly alter cell surface expression levels of the AD relevant proteins suggests that the involvement of LRP/LR in the amyloidogenic process may be independent of gene expression modulation and possibly entails receptor interactions with the said proteins.

In an attempt to elucidate the mechanism by which LRP/LR influences the amyloidogenic pathway, sAPPβ levels were assessed post antibody (FIG. 2d) and shRNA treatment (FIG. 4d). Upon a dose dependent administration of IgG1-iS18, a significant reduction in sAPPβ levels was observed across all antibody concentrations (56.29%, 69.35%, 92.42% and 99.76% for 25 μg/ml, 50 μg/ml, 75 μg/ml and 100 μg/ml respectively). Similar results were obtained for shRNA1 mediated LRP/LR downregulated HEK293 cells (FIG. 4d).

Figure 6A:
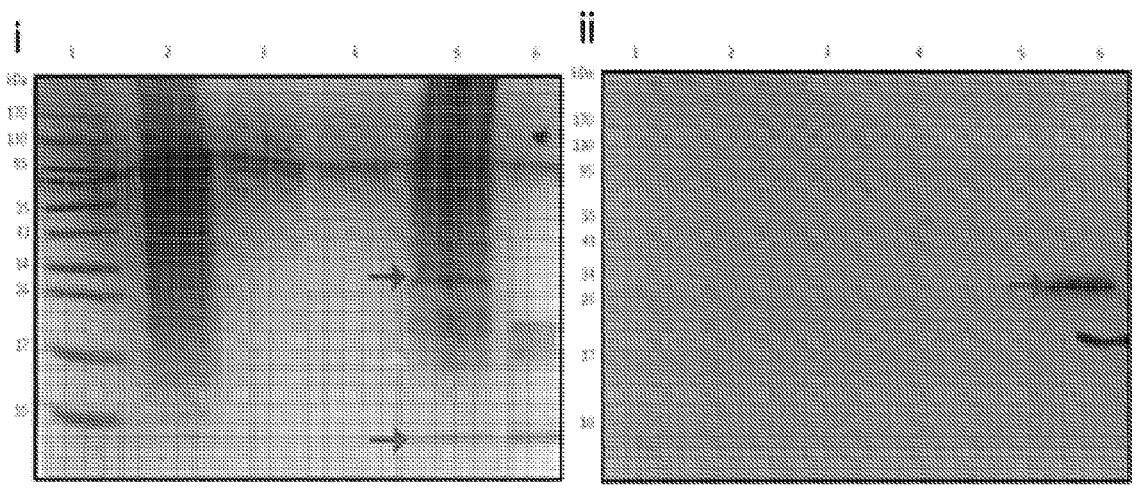
FIG. 6a(i) shows a pull down assay of cell lysates containing recombinantly expressed LRP/LR::FLAG co-incubated with exogenous Aβ.
Figure 7:
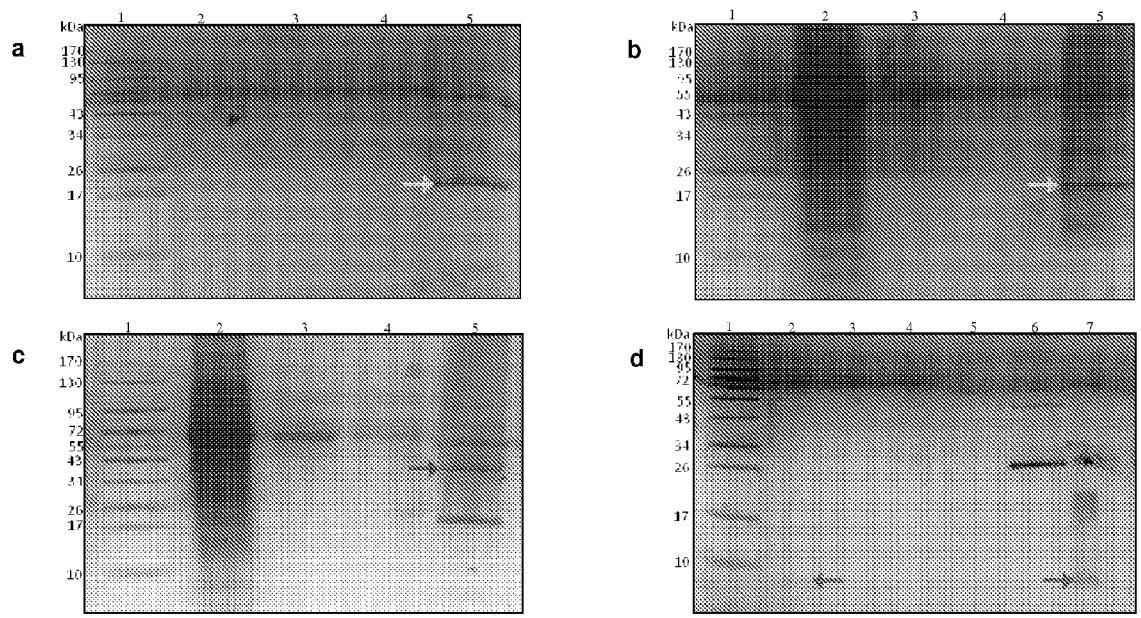
FIG. 7 shows post pull down assay protein detection of control samples.

Following the above, pull down assays were conducted to examine whether LRP/LR (recombinantly expressed fused to a FLAG tag) and 100 ng/ml exogenously applied synthetic Aβ$_{42}$ (Sigma-Aldrich) (which mimics augmented concentrations of soluble Aβ$_{42}$ present in AD brains) form stable interactions. The presence of both proteins in eluted samples (FIG. 6a, i—lane 6) implies that such an association exists. The identity of LRP/LR was further confirmed by immunoblotting (FIG. 6a, ii). Relevant controls are shown in FIG. 7 discussed below.

In general, FIG. 6 shows LRP/LR as an Aβ interacting protein and the cell rescuing effects of anti-LRP/LR antibody IgG1-iS18. FIG. 6a (i) shows that a FLAG® Immunoprecipitation kit (Sigma Aldrich) was employed to perform a pull down assay of cell lysates containing recombinantly expressed LRP/LR::FLAG co-incubated with exogenous Aβ. Lane 1: Molecular weight marker; lane 2: unbound sample; lanes 3-4: washes; lane 5: eluted sample and lane 6: 2 μg of synthetic Aβ42 (positive control).

FIG. 6a (ii) shows experimental results where Immunoblot was employed to validate the position of LRP::FLAG (38 kDa).

FIG. 6b shows cellular viability of HEK293 cells, as determined by (3-(4,5-dimethylthiazol-2-yl)-2,5-diphenyltetrazolium bromide (MTT) (1 mg/ml) assay, post exogenous treatment with synthetic Aβ$_{42}$ and upon co-incubation with anti-LRP/LR IgG1-iS18 or IgG1-HD37 (negative control). The cell viability was assessed 48 h post treatment and the no antibody control was set to 100%. SH-SY5Y (as shown in FIG. 6c) and N2a cells (as shown in FIG. 6d) were exposed to similar treatments. It can be seen that the co-incubation with anti-LRP/LR IgG1-iS18 significantly enhanced cell viability.

FIG. 6e shows cellular proliferation of N2a cells as determined by colorimetric 5-bromo-2'-deoxyuridine (BrdU) non-isotopic immunoassay (Calbiochem®), allowing 4 h for BrdU incorporation into cultured cells. Error bars represent sd. **$p<0.01$; Student's t-test.

FIG. 7 shows the results of pull down assay protein detection of control samples. Pull down assays were employed to investigate the proteins detectable in unbound samples (lane 2), wash steps (lanes 3 and 4) and eluted samples (FIG. a-c, lane 5, FIG. d, lane 6). Figures represent anti-FLAG® M2 beads incubated with (a) lysis buffer, (b) non-transfected HE293 cell lysates, (c) HEK293 cell lysates of cells transfected with pCIneo::FLAG as well as (d) pure synthetic Aβ$_{42}$ in the absence of cell lysate. Lane 7 of (d) represents 2 μg of synthetic Aβ$_{42}$ which serves as a positive control. Samples were resolved on 16% Tris-tricine SDS PAGE gels and stained with Coomassie Brilliant Blue. Blue, red and green arrows are indicative of Aβ$_{42}$, LRP::FLAG and anti-FLAG M2 agarose beads, respectively.

In summary, exogenous application of 200 nM and 500 nM Aβ$_{42}$ significantly reduced cell viability in HEK293 cells (FIG. 6b). Co-incubation of cells with 50 μg/ml anti-LRP/LR specific antibody IgG1-iS18 and 500 nM Aβ$_{42}$ (the concentration at maximal cytotoxic effects were observed) significantly enhanced cell viability (FIG. 6b). Similar results, albeit at different A$\beta_{42}$ concentrations were observed for SH-SY5Y (FIG. 6c) and N2a (FIG. 6d) cells. The reduction in cell viability observed in N2a cells (FIG. 6d) was later shown to be as a result of reduced cellular proliferation (FIG. 6e). It is shown that LRP/LR may be implicated in A$\beta_{42}$ mediated cytotoxicity and that the identified association (direct or indirect) may be pathological in nature.

Animal Trials for Validation of Anti-LRP/LR Specific Antibodies in the Treatment Alzheimer's Disease (AD)

LRP/LR plays a definitive role in the in A$\beta$ mediated pathogenesis in AD, as proposed by the above in vitro data above. It has been shown in vitro that IgG1-iS18 (LRP/LR specific antibody) plays an important role in modulation of LRP/LR and the modulation of the concentrations of Alzheimer's Disease (AD) relevant proteins amyloid precursor protein (APP), beta ($\beta$) and gamma ($\gamma$) secretases and amyloid beta peptide (A$\beta$). It is further proposed that the antibodies and/or shRNAs described above may rescue neurons from A$\beta$ mediated cell death or impede their proliferation.

Animal trials probing the potential of these antibodies and/or shRNAs as an AD therapeutic will be initiated and conducted. Transgenic AD mice harbouring human transgenes with 5 AD related mutations (3 mutations in the APP protein and 2 in the PSEN1 enzymatic subunit of $\gamma$-secretase) (The Jackson Laboratory, strain: B6SJL-Tg (APPSwF|Lon, PSEN1*M146L*L286V)6799Vas|Mmjax) will be employed. Transgenic animals (caged in individual cages in a temperature controlled environment) will be divided into six groups (5 mice/group). Ten wild-type mice per treatment will serve as phenotype controls.

These 5x-Tg-AD mice develop pathological features mimicking the human condition within 4 months, namely: plaque deposition, synaptic and neuronal loss as well as cognitive deficits.

The antibodies and shRNA described above will be utilized in any such animal experimentation. Particularly, anti-LRP/LR antibody, IgG1-iS18, or IgG1-HD37 (negative control) (50 µg/ml) will be stereotaxically administered as a single intracerebroventricular (ICV) injection either prior to plaque deposition (<4 months) or post plaque deposition (4 months). Antibodies will be administered into the third ventricle (due to its proximity to the hippocampus). Age matched transgenic mice receiving ICV injections of the vehicle shall serve as controls. At varying weekly time intervals, groups of mice will be tested for deficits in spatial learning by means of the Morris Water Maze Test. Two days prior to euthanization, the final Morris Water Maze Test shall be performed. Mice will be euthanized by transcardial perfusion with ice-cold saline followed by 4% buffered paraformaldehyde (in saline solution). Approximately 18-20 hippocampal sections (35 µm thickness) per animal (from both hemispheres) will be collected and immunohistochemical methods (anti-A$\beta$ antibodies) employed to assess total A$\beta$ levels and Congo Red staining used to detect plaque deposits on these sections (as detailed by Chauhan and Siegel, 2003). To ensure antibody administration did not cause cerebral damage and haemorrhaging sections shall be stained for haemosiderin using Prussian blue.

CONCLUSION

The results for the in vitro experiments indicate that LRP/LR co-localises with all the relevant AD proteins (APP, $\beta$ and $\gamma$-secretase as well as A$\beta$) and consequently implies that an association between these proteins and the receptor may exist, as was further validated by pull down assay methodology with respect to the neurotoxic A$\beta_{42}$ peptide. In addition, receptor blockage and/or downregulation of LRP/LR effectively impeded A$\beta$ shedding affirming the importance of the receptor in the amyloidogenic process. Interestingly, LRP/LR blockage did not result in modulation of cell surface proteins central to the amyloidogenic process, thereby inferring that the influence of LRP/LR may rather be as a result of protein interactions. The observed decrease in sAPP$\beta$ levels post antibody and shRNA treatment suggests that LRP/LR exerts its affects via $\beta$-secretase. LRP/LR was further implicated in A$\beta$ induced cytotoxicity and the interaction may possibly result in aberrant proliferative cell signalling pathways. In conclusion, our findings suggests that the LRP/LR is implicated in AD's pathogenesis and recommends anti-LRP/LR specific antibodies and shRNAs as possible alternative therapeutic tools for AD treatment.

While the invention has been described and/or illustrated and/or exemplified in detail with respect to specific embodiments and/or examples thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and equivalents thereto.

REFERENCES

1 Maloney, B. & Lahiri, D. K. The Alzheimer's amyloid beta-peptide (Abeta) binds a specific DNA Abeta-interacting domain (AbetaID) in the APP, BACE1, and APOE promoters in a sequence-specific manner: characterizing a new regulatory motif. Gene 488, 1-12, doi:S0378-1119 (11)00262-9 [pii] 10.1016/j.gene.2011.06.004 (2011).

2 Da Costa Dias, B., Jovanovic, K., Gonsalves, D. & Weiss, S. F. Structural and mechanistic commonalities of amyloid-beta and the prion protein. Prion 5, 126-137, doi: 17025 [pii] (2011).

3 Verdier, Y. & Penke, B. Binding sites of amyloid beta-peptide in cell plasma membrane and implications for Alzheimer's disease. Curr Protein Pept Sci 5, 19-31 (2004).

4 Mount, C. & Downton, C. Alzheimer disease: progress or profit? Nat Med 12, 780-784, doi:nm0706-780 [pii] 10.1038/nm0706-780 (2006).

5 Gonsalves, D., Jovanovic, K., Da Costa Dias, B. & Weiss, S. F. Global Alzheimer Research Summit Basic and clinical research: Present and future Alzheimer research. Prion 6, doi:18854 [pii] (2012).

6 Busciglio, J., Lorenzo, A., Yeh, J. & Yankner, B. A. beta-amyloid fibrils induce tau phosphorylation and loss of microtubule binding. Neuron 14, 879-888, doi:0896-6273 (95)90232-5 [pii] (1995).

7 Dias Bda, C, Jovanovic, K., Gonsalves, D. & Weiss, S. F. Structural and mechanistic commonalities of amyloid-beta and the prion protein. Prion 5, 126-137, doi: 17025 [pii] 10.4161/pri.5.3.17025 (2011).

8 Sepulveda, F. J., Parodi, J., Peoples, R. W., Opazo, C. & Aguayo, L. G. Synaptotoxicity of Alzheimer beta amyloid can be explained by its membrane perforating property. PLoS One 5, e11820, doi:10.1371/journal.pone.0011820 (2010).

9 Parkin, E. T. et al. Cellular prion protein regulates beta-secretase cleavage of the Alzheimer's amyloid precursor protein. Proc Natl Acad Sci USA 104, 11062-11067, doi: 0609621104 [pii] 10.1073/pnas.0609621104 (2007).

10 Vincent, B., Sunyach, C, Orzechowski, H. D., St George-Hyslop, P. & Checker, F. p53-Dependent transcriptional control of cellular prion by presenilins. J Neurosci 29, 6752-6760, doi:29/20/6752 [pii] 10.1523/JNEUROSCI.0789-09.2009 (2009).

11 Kellett, K. A. & Hooper, N. M. Prion protein and Alzheimer disease. Prion 3, 190-194, doi:9980 [pii] (2009).

12 Lauren, J., Gimbel, D. A., Nygaard, H. B., Gilbert, J. W. & Strittmatter, S. M. Cellular prion protein mediates impairment of synaptic plasticity by amyloid-beta oligomers. Nature 457, 1128-1132, doi:nature07761 [pii] 10.1038/nature07761 (2009).

13 Kudo, W. et al. Cellular prion protein is essential for oligomeric amyloid-beta-induced neuronal cell death. Hum Mol Genet 21, 1138-1144, doi:ddr542 [pii] 10.1093/hmg/ddr542 (2012).

14 Resenberger, U. K., Winklhofer, K. F. & Tatzelt, J. Cellular Prion Protein Mediates Toxic Signaling of Amyloid Beta. Neurodegener Dis, doi:000332596 [pii] 10.1159/000332596 (2011).

15 Castillo, G. M. et al. Laminin inhibition of beta-amyloid protein (Abeta) fibrillogenesis and identification of an Abeta binding site localized to the globular domain repeats on the laminin a chain. J Neurosci Res 62, 451-462, doi: 10.1002/1097-4547(20001101)62:3<451::AID-JNR15>3.0.CO; 2-F [pii] (2000).

16 Koo, E. H., Park, L. & Selkoe, D. J. Amyloid beta-protein as a substrate interacts with extracellular matrix to promote neurite outgrowth. Proc Natl Acad Sci USA 90, 4748-4752 (1993).

17 Mbazima, V., Da Costa Dias, B., Omar, A., Jovanovic, K. & Weiss, S. Interactions between PrPc and other ligands with the 37-kDa/67-kDa laminin receptor. Frontiers in Bioscience 15, 1150-1163 (2010).

18 Omar, A. et al. Patented biological approaches for the therapeutic modulation of the 37 kDa/67 kDa laminin receptor. Expert Opin Ther Pat 21, 35-53, doi:10.1517/13543776.2011.539203 (2011).

19 Gauczynski, S. et al. The 37-kDa/67-kDa laminin receptor acts as the cell-surface receptor for the cellular prion protein. EMBO J 20, 5863-5875, doi:10.1093/emboj/20.21.5863 (2001).

20 Gauczynski, S. et al. The 37-kDa/67-kDa laminin receptor acts as a receptor for infectious prions and is inhibited by polysulfated glycanes. J Infect Dis 194, 702-709, doi: JID36299 [pii] 10.1086/505914 (2006).

21 Zuber, C. et al. Invasion of tumorigenic HT1080 cells is impeded by blocking or downregulating the 37-kDa/67-kDa laminin receptor. J Mol Biol 378, 530-539, doi:S0022-2836(08)00164-2 [pii] 10.1016/j.jmb.2008.02.004 (2008).

The invention claimed is:

1. A method for reducing the concentration of amyloid beta peptide (Aβ) in a human or animal suffering from Alzheimer's Disease (AD), the method comprising:
    contacting 37 kDa/67 kDa laminin receptor (LRP/LR) with shRNA 1 having sequence listing as set forth in SEQ ID NO: 1, such that binding occurs between mRNA of 37 kDa/67 kDa laminin receptor (LRP/LR) and shRNA 1 causing a downregulation in 37 kDa/67 kDa laminin receptor (LRP/LR) which in turn causes a decrease in the concentration of amyloid beta peptide (Aβ) in said human animal.

2. The method according to claim 1, further comprising contacting the 37 kDa/67 kDa laminin receptor (LRP/LR) with shRNA 7 having sequence listing as set forth in SEQ ID NO: 2.

3. A method for reducing the concentration of amyloid beta peptide (Aβ) in a human or animal suffering from Alzheimer's Disease (AD), the method comprising:
    contacting 37 kDa/67 kDa laminin receptor (LRP/LR) with anti-37 kDa/67 kDa laminin receptor (LRP/LR) specific antibody, and
    contacting 37 kDa/67 kDa laminin receptor (LRP/LR) with shRNA1 having sequence listing as set forth in SEQ ID NO: 1,
    such that binding occurs between a surface epitope of 37 kDa/67 kDa laminin receptor (LRP/LR) and anti-37 kDa/67 kDa laminin receptor (LRP/LR) specific antibody causing a decrease in the concentration of amyloid beta peptide (Aβ), and
    such that binding occurs between mRNA of 37 kDa/67 kDa laminin receptor (LRP/LR) and shRNA1 causing a down regulation in the 37 kDa/67 kDa laminin receptor (LRP/LR) which in turn causes a decrease in the concentration of amyloid beta peptide (Aβ) in said human or animal.

4. The method according to claim 3, further comprising contacting the 37 kDa/67 kDa laminin receptor (LRP/LR) with shRNA 7 having sequence listing as set forth in SEQ ID NO: 2.

* * * * *

SEQUENCE LISTING

```
<160> NUMBER OF SEQ ID NOS: 2

<210> SEQ ID NO 1
<211> LENGTH: 21
<212> TYPE: RNA
<213> ORGANISM: Homo sapiens

<400> SEQUENCE: 1
gcucgugcaa uuguugccau u                                              21

<210> SEQ ID NO 2
<211> LENGTH: 21
<212> TYPE: RNA
<213> ORGANISM: Homo sapiens

<400> SEQUENCE: 2
ggcagugacc aaggaggaau u                                              21
```